(12) United States Patent
Chuang et al.

(10) Patent No.: US 7,211,702 B2
(45) Date of Patent: May 1, 2007

(54) PROCESS FOR PRODUCTION OF ALCOHOLS

(75) Inventors: Karl T. Chuang, Edmonton (CA); Yung F. Chen, Taoyuan (TW)

(73) Assignee: The Governors of the University of Alberta, Edmonton, Alberta (CA)

( * ) Notice: Subject to any disclaimer, the term of this patent is extended or adjusted under 35 U.S.C. 154(b) by 725 days.

(21) Appl. No.: 10/705,919

(22) Filed: Nov. 13, 2003

(65) Prior Publication Data

US 2004/0167365 A1  Aug. 26, 2004

Related U.S. Application Data

(62) Division of application No. 09/918,474, filed on Aug. 1, 2001, now Pat. No. 6,833,483.

(60) Provisional application No. 60/261,203, filed on Jan. 16, 2001.

(51) Int. Cl.
*C07C 29/04* (2006.01)

(52) U.S. Cl. ............... 568/895; 568/896; 568/898; 568/899; 568/900; 568/901

(58) Field of Classification Search ............. 568/895, 568/896, 898, 899, 900, 901
See application file for complete search history.

(56) References Cited

U.S. PATENT DOCUMENTS

| | | | |
|---|---|---|---|
| 3,280,014 | A | 10/1966 | Kordesch et al. |
| 3,948,681 | A | 4/1976 | Burger, Jr. et al. |
| 4,469,903 | A | 9/1984 | Schmidt |
| 4,760,202 | A | 7/1988 | Dettmer et al. |
| 4,760,203 | A | 7/1988 | Carls et al. |
| 4,911,803 | A | 3/1990 | Kunz |
| 4,982,022 | A | 1/1991 | Smith, Jr. et al. |
| 5,221,441 | A | 6/1993 | Smith, Jr. |
| 5,488,185 | A | 1/1996 | Ramachandran et al. |

FOREIGN PATENT DOCUMENTS

WO    WO 99/44253    9/1999

OTHER PUBLICATIONS

Azeotropic and Extractive Distillation, Interscience Library of Chemical Engineering and Processing, John Wiley and Sons, New York (1964), pp. 165-168 and 179-203.
WANKAT in Equilibrium Slaged Separations, Elsevier, New York (1988); pp. 301-335.
Linnekoski et al. in Applied Catalysis A: General, vol. 170 (1998), pp. 117-126.
Gonzalez et al., Industrial and engineering Chemistry Research, 1997, 36, 3845-3853.
Hydrocarbon Processing, Nov. 1972, pp. 113-116.
Odioso et al., Industrial and Engineering Chemistry, Mar. 1961, vol. 53(3), pp. 209-211.
Kishimoto, Hirotatsu et al; Amorphous Alloy Electrodes for Electrooxidation of Propane; Chemical Abstract accession No. 123: 125466; XP-002193071; abstract, (1987).

*Primary Examiner*—Elvis O. Price
(74) *Attorney, Agent, or Firm*—Philip C. Mendes da Costa; Bereskin & Parr

(57) ABSTRACT

The invention disclosed relates to the production of alcohols. A first aspect of the invention relates to a process for production of alcohols, and in particular to a process for the catalytic hydration of an olefin to the corresponding alcohol in substantially anhydrous form, under selected mild reaction conditions, and using a selected catalyst. A second aspect of the invention relates to a process for dehydration of an azeotropic mixture, including a first alcohol and water. A hydration reaction between the water in the azeotropic mixture and an added olefin, under selected mild conditions, and using a selected catalyst, produces a product including a second alcohol corresponding to the olefin, and the first alcohol, in substantially anhydrous form.

15 Claims, 14 Drawing Sheets

PROCESS FOR PRODUCTION OF ALCOHOLS

This application is a divisional of U.S. patent application Ser. No. 09/918,474 filed on Aug. 1, 2001 now U.S. Pat. No. 6,833,483.

FIELD OF THE INVENTION

A first aspect of the present invention relates to a process for production of alcohols, and in particular to a process for the catalytic hydration of an olefin to the corresponding alcohol.

A second aspect of the present invention relates to a process for dehydration of an azeotropic mixture including a first alcohol and water to produce the first alcohol in a substantially anhydrous state.

BACKGROUND OF THE INVENTION

Several processes are known for the conversion of ethylene, higher olefins, and combinations of olefins to the corresponding alcohol by a hydration reaction. Typically, the hydration reaction produces a product mixture comprising an alcohol and an ether, each having the same carbon chain length as the olefin, in equilibrium with the olefin and water or steam. The thermodynamics and hence the equilibrium of the hydration reaction is such that formation of the alcohol and ether product mixtures is more favourable at low temperatures and high pressures. The attainment of the equilibrium is promoted through the use of a hydration catalyst. Capital and operating costs are lower when the hydration reaction is performed under mild conditions, however the equilibrium amount of the alcohol in the reaction mixture at low temperature and pressure is lower than the equilibrium amount of alcohol in the reaction mixture at low temperature and high pressure.

Examples of such prior art processes include Rolf-Rainer et al. in U.S. Pat. No. 4,760,203, issued in 1988, which describes the production of isopropanol, also known as IPA or 2-propanol or isopropyl alcohol, by hydration of a propene-containing hydrocarbon stream using an acidic cation exchange resin catalyst and a series of interconnected reactors in series. In each of the reactors an aqueous stream and a parallel hydrocarbon stream flow in opposite directions, thereby effecting separation of a product isopropanol rich stream from the reaction mixture. Dettmar et al. in U.S. Pat. No. 4,760,202, issued in 1988, describe the hydration of isoolefins having 4 or 5 carbon atoms to produce tertiary alcohols using a counterflow process and a hydration catalyst. Ramachandran and Dao in U.S. Pat. No. 5,488,185, issued in 1996, describe the hydration of an olefin in a mixture with an alkane to the corresponding alcohol in the presence of a hydration catalyst. Schmidt in U.S. Pat. No. 4,469,903, issued in 1984, describes a process for the production of an aliphatic alcohol, and in particular isopropanol, by the direct hydration of an olefinic hydrocarbon. The product alcohol in the equilibrium mixture is recovered from a water-rich hydration zone effluent stream by countercurrent liquid-liquid extraction against a paraffinic solvent.

Smith, Jr. in U.S. Pat. No. 5,221,441, issued in 1993, describes a method for operating a distillation process for three particular chemical production processes. One of said processes is the production of tertiary butanol, also known as tertiary butyl alcohol, by the hydration of isobutene, also known as 2-methylpropene or isobutylene, using an acid cation exchange resin. The acid cation exchange resin must be maintained in a wetted state by contact with water present in a liquid phase to maintain catalytic selectivity. When the acid cation exchange catalyst is not in contact with the liquid phase the catalyst loses selectivity to tertiary butanol due to loss of water.

In each of the above processes the catalyst is characteristically a hydrophilic acidic hydration catalyst. Further, in each of the above processes the product is wet, and at least one additional refining step is required for recovery of anhydrous liquid product.

Recovery of an alcohol in a substantially anhydrous state from an azeotropic mixture with water is an expensive and complex component of many industrial processes for the production of the alcohol.

As described above, several processes are known for the conversion of an olefin to the corresponding alcohol by a hydration reaction. Typically, the hydration reaction produces an alcohol, or a product mixture comprising a mixture of said alcohol and an ether, the alcohol and the ether each having the same carbon chain length as the olefin, in equilibrium with the olefin and water. The thermodynamics and hence the equilibrium of the hydration reaction is such that formation of the alcohol is more favorable at low temperatures and high pressures. The attainment of the equilibrium is promoted through use of a hydration catalyst. Although capital and operating costs are lower when the hydration reaction is performed under mild conditions, the equilibrium amount of the alcohol in the reaction mixture at low pressures is lower than the equilibrium amount of alcohol in the reaction mixture at high pressures. Several catalysts having acidic properties are useful for the hydration of an olefin to the corresponding alcohol. Said catalysts include acidic cation exchanged resins, inorganic acids and acids supported on inorganic supports. All such prior art catalysts are hydrophilic.

Alcohols are often sold in different grades, depending on the level of water they contain. For example, industrial ethanol has approximately 96.5% (vol) ethanol, the balance being water and a small amount of crude pyridine to "denature" the material, and sometimes a colouring agent. Denatured spirit has 88% (vol) ethanol, water and denaturing compounds. Fine alcohol (96.0–96.5% vol ethanol) is not denatured because it is used in preparation of pharmaceuticals, cosmetics and products for human consumption. Absolute alcohol must have at least 99.7–99.8% vol ethanol, and is used in the preparation of pharmaceuticals and products for human consumption. Normally, absolute alcohol is sold with over 99.9% vol ethanol. Conventional processes for production of ethanol, isopropanol and other alcohols by hydration of an olefin produce a product mixture containing both said alcohol and water. Therefore several methods have been developed by which fine or absolute grades of the alcohol can be recovered from the product mixture. Each such method is costly, with the consequence that fine and absolute grades of alcohol are significantly more expensive to produce than grades containing higher amounts of water.

One prior art approach is to separate a product mixture containing an alcohol and water using a third liquid that selectively removes the alcohol from the product mixture by absorption of the alcohol in the third liquid. Examples of such processes for recovery of light alcohols are described by Rolf-Rainer et al. in U.S. Pat. No. 4,760,203, issued in 1988, by Dettmar et al. in U.S. Pat. No. 4,760,202, issued in 1988, and by Schmidt in U.S. Pat. No. 4,469,903, issued in 1984.

Another prior art approach is first to distill the alcohol from the product mixture as an azeotropic mixture containing said alcohol and water. The water is then removed from the azeotropic mixture by use of a third fluid that also forms an azeotropic mixture with water. The volatile third component is added to the azeotropic mixture of alcohol and water. The mixture is then separated by distillation, the third component forming an azeotropic mixture with water that has a boiling point lower than a boiling point of the azeotropic mixture of the alcohol and water. The third component and the water are thereby distilled from the mixture to leave the alcohol as a liquid product having a water content lower than a water content of the original azeotropic mixture. Separation of azeotropic mixtures is described, for example, by Hoffman in *Azeotropic and Extractive Distillation, Interscience Library of Chemical Engineering and Processing*, John Wiley and Sons, New York (1964), pages 165–168 and 179–203 and by Wankat in *Equilibrium Staged Separations*, Elsevier, New York (1988).

Normally, hydration under mild conditions of an olefin having a carbon chain length of at least 4 carbon atoms produces the corresponding alcohol, but only negligible or undetectably small amounts of the corresponding ether. Linnekoski et al. in Applied Catalysis A: General, vol. 170 (1998), pages 117–126, measured and compared the activation energies for hydration of isoamylenes (2-methyl-1-butene and 2-methyl-2-butene) to form 2-methyl-2-butanol (t-amyl alcohol) and etherification of the same isoamylenes with ethanol to form ethyl (2-methyl-2-butyl) ether (ethyl t-amyl ether). The activation energy for the etherification reaction was 117.7 kJ.mol-1, which value is considerably greater than the activation energy for the hydration reaction of the same olefins to 2-methyl-2-butanol, 79.9 kJ.mol-1. Thus it is to be expected that there will be negligibly small conversion of 2-methyl-2-butenes to di-(2-methyl-2-butyl) ether (di-t-amyl ether) during hydration of 2-methyl-2-butenes to 2-methyl-2-butanol under mild conditions

SUMMARY OF THE INVENTION

The first aspect of the invention provides a process by which an olefin can be hydrated to produce a corresponding alcohol under mild conditions, more efficiently and more economically than can be achieved using the prior art processes. It is desirable that the alcohol is recovered as a substantially anhydrous product. It is even more desirable that the alcohol is recovered as a substantially anhydrous liquid product. The present invention provides a process for the continuous and simultaneous catalytic hydration of an olefin under mild conditions to a reaction mixture containing the corresponding alcohol and recovery of the alcohol as a substantially anhydrous liquid product from the reaction mixture.

The second aspect of the invention provides a process by which water can be removed easily from an azeotropic mixture of an alcohol and water to allow recovery of the corresponding substantially anhydrous alcohol under mild conditions, more efficiently and more economically than can be achieved using the prior art processes. This aspect of the present invention provides a process for the continuous removal of the water content of an azeotropic mixture containing a first alcohol and water by catalytic hydration of an olefin under mild conditions to a corresponding second alcohol, with simultaneous and continuous removal of the first alcohol and the second alcohol from the reaction mixture. In one embodiment, the hydration reaction is carried out using a solid phase hydration catalyst e.g. in a catalytic distillation column that serves simultaneously as a reactor and as a distillation column.

According to one embodiment of the invention, a process for producing an alcohol is provided, comprising:
a) subjecting an olefin to a hydration reaction with water to form a reaction product including the corresponding alcohol, the olefin having a carbon chain length in the range of 2 to 12 carbon atoms, the carbon chain being selected from a linear chain, a branched chain and a chain having a cyclic hydrocarbon component, the reaction being conducted in the presence of a solid state olefin hydration catalyst, the temperature and pressure of the hydration reaction being selected so that the olefin is largely in a vapour phase and the alcohol is in the liquid phase the olefin being in a molar excess when compared with water, and
b) simultaneously recovering the alcohol as a substantially anhydrous liquid.

In some aspects of this embodiment of the invention, it is advantageous to employ a catalyst having hydrophobic properties.

In some cases, the hydration reaction is a catalytic distillation reaction, which can be effected in a distillation column, the olefin and water being continuously fed to the column. The catalyst may be disposed in a single catalyst bed or in several beds. As will be apparent below, there is advantage in providing exposure to the catalyst in two separate spaced apart beds. The beds may be fixed beds. The catalyst beds are typically disposed within the same reactor/distillation column.

Although not specifically described herein, it will be appreciated by those skilled in the art that the olefin may include a cyclic hydrocarbon component.

According to another embodiment of the invention, a process for reducing the water content of an azeotropic mixture of a first alcohol and water is provided, comprising:
(a) effecting a hydration reaction of the water content of the azeotropic mixture with an olefin, wherein the olefin is hydrated to a corresponding second alcohol, the second alcohol being selected from the group consisting of the same alcohol as the first alcohol, an alcohol readily separable from the first alcohol by a distillation procedure, and an alcohol forming a useful mixture when mixed with the first alcohol, the hydration reaction of the olefin being conducted in the presence of a solid state hydration catalyst, the temperature and the pressure of the hydration reaction being selected so that the olefin is largely in the vapour phase and the first alcohol and the second alcohol are each largely in a liquid phase, the olefin being in a molar excess when compared with the water content of the azeotropic mixture, and
(b) continuously removing the first alcohol and the second alcohol as a substantially anhydrous liquid mixture.

The catalyst is typically disposed in at least two spaced apart catalyst beds. The catalytic beds are typically disposed within the same reactor/distillation column, although in some cases a pre-reactor with a bed and then a column having a bed, can be used. One bed will work, albeit not as well.

In some aspects of this embodiment of the invention, it is advantageous to employ a catalyst having hydrophobic properties.

In one aspect of this embodiment of the invention, the hydration reaction is a catalytic distillation reaction, which can be effected in a distillation column, the olefin and the azeotropic mixture being continuously fed to the column.

BRIEF DESCRIPTION OF THE DRAWINGS

These and the other features of the invention will become more apparent from the following description in which reference is made to the appended drawings, wherein.

DETAILED DESCRIPTION OF THE INVENTION

Figure 1:
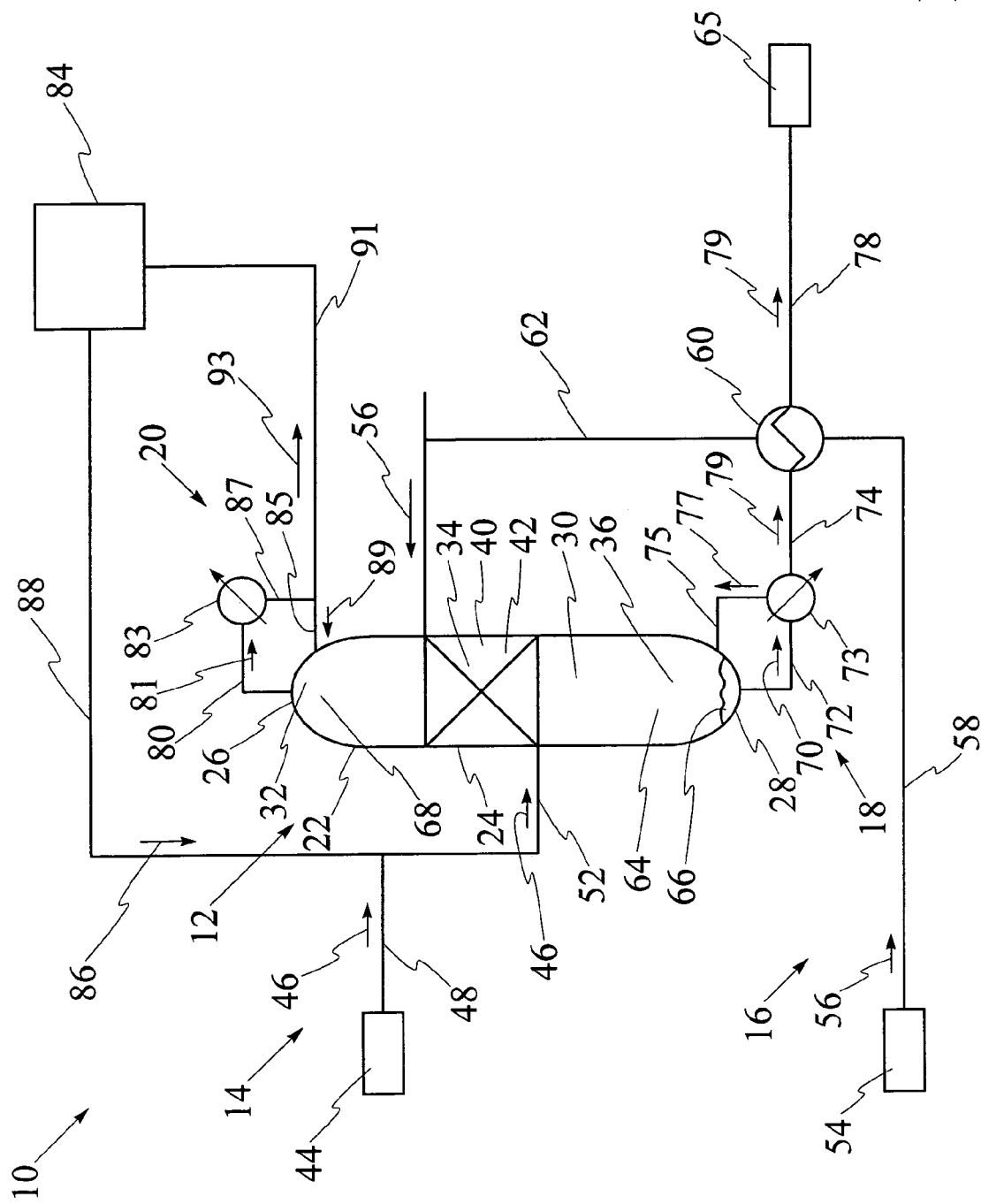
FIG. 1 is a schematic diagram of a catalytic distillation process for hydration of an olefin to the corresponding alcohol, in which the catalytic distillation column has one catalyst bed.

According to the first aspect of the invention, the hydration reaction is carried out using a solid phase hydration catalyst in a catalytic distillation column that serves simultaneously as a reactor and as a distillation column. When a reaction product mixture is separated continuously by distillation simultaneously with the reaction, the process is termed "reactive distillation." When a catalyst is used to catalyze the reaction occurring simultaneously with distillation the process is termed "catalytic distillation." In the present invention an olefin and water are continuously fed to the catalytic distillation column. The reaction is performed at a temperature and a pressure selected so that the rate of the reaction is high, the olefin is in the vapour phase, and the alcohol corresponding to the olefin i.e. having the same linear or branched structure and the same number of carbon atoms is recoverable as a liquid product. The alcohol is continuously removed from the reaction mixture as a liquid product stream from the base of the catalytic distillation column. The operating conditions can be selected so that the alcohol content of the liquid product stream is over 99% and as high as 99.9%, i.e. the alcohol is recovered as a substantially anhydrous liquid product. Exemplary ranges for T and P are P=0.1–4 MPa and T=50–225° C.)

For example, hydration of ethylene produces ethanol and diethyl ether in an equilibrium reaction illustrated as Equation 1. Hydration of an olefin with more than two carbon atoms produces a corresponding secondary alcohol and an ether as illustrated in Equation 2 in which R represents an organic radical having one or more carbon atoms. The proportion of alcohol to ether in the equilibrium mixture depends on the reaction conditions and on the relative proportions of water and olefin in the reaction mixture.

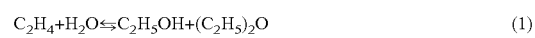
$$C_2H_4 + H_2O \rightleftharpoons C_2H_5OH + (C_2H_5)_2O \quad (1)$$

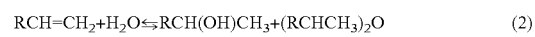
$$RCH=CH_2 + H_2O \rightleftharpoons RCH(OH)CH_3 + (RCHCH_3)_2O \quad (2)$$

The characteristics of a process by which amyl alcohol has been produced using a catalytic distillation column and AMBERLIST 15 as a catalyst have been studied by Gonzalez et al. (*Industrial and Engineering Chemistry Research*, 1997, 36, 3845–3853). The study by Gonzalez et al. did not include an advantage of the present invention, which is described below. In particular, the present invention includes the advantages of using dual spaced apart catalyst beds, and use of a hydration catalyst having hydrophobic characteristics, that will now be described for the first time.

The equipment and method for the simultaneous hydration of an olefin to a corresponding secondary alcohol and recovery of the alcohol will now be described with reference to FIGS. 1 through 5. The invention will then be illustrated using a series of non-limiting examples to illustrate procedures and conditions applicable to specific alcohols, with reference to FIGS. 1 through 13.

The present invention provides a method for the continuous and simultaneous catalytic hydration of an olefin to a product mixture rich in an alcohol corresponding to the olefin, and removal of the product mixture rich in alcohol from the reaction mixture. A first embodiment of equipment 10 for said method for hydration of an olefin to the corresponding alcohol will be described with reference to FIGS. 1 and 2. A second embodiment of equipment 100 for said process will be described with reference to FIGS. 3 and 4. A component that is common to each of first embodiment of equipment 10 and second embodiment of equipment 100 will be identified using the same reference numeral. One PRIOR ART process for the hydration of an olefin to the corresponding alcohol is illustrated in FIG. 5, for purpose of comparison with the process of the present invention.

Referring to FIG. 1, first embodiment of equipment 10 for continuous and simultaneous hydration of an olefin to a corresponding alcohol and recovery of said alcohol as a liquid product comprises a catalytic distillation column 12, an olefin feed system 14, a water feed system 16, a liquid product recovery system 18, and a volatiles recovery system 20.

Figure 2:
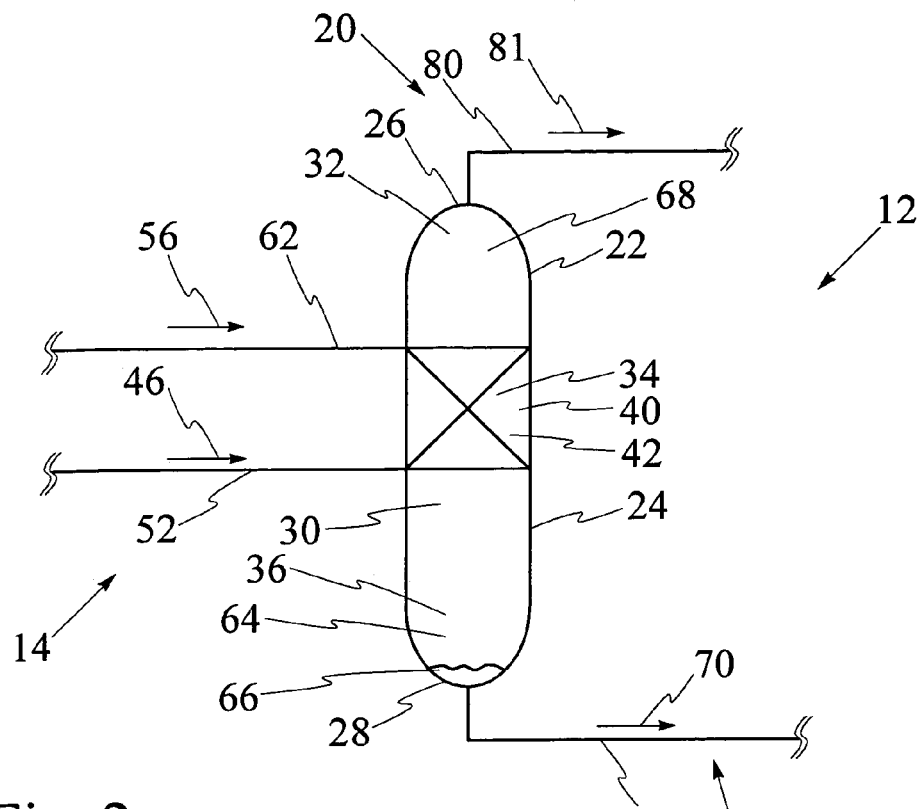
FIG. 2 is a schematic diagram of a catalytic distillation column having one catalyst bed for the catalytic distillation process shown in FIG. 1.

Referring to FIG. 2, catalytic distillation column 12 has a body 22 having elongate cylindrical sidewalls 24, a top 26 and a base 28 defining an interior cavity 30. Body 22 is constructed of a material that is unaffected by the components of a reaction mixture contained within interior cavity 30. Body 22 can be insulated so as to maintain and withstand a temperature at which a reaction is conducted within interior cavity 30. Body 22 is capable of containing a pressurized reaction mixture at a pressure at which the reaction is conducted. Interior cavity 30 has a first portion 32, a second portion 34, and a third portion 36. Second portion 34 serves as a reaction zone during a catalytic distillation process. At least one catalyst bed 40 is situated within second portion 34. Catalyst bed 40 contains packed material comprising an active olefin hydration catalyst 42. Rectification of the volatile components of the reaction mixture occurs in first portion 32 during the catalytic distillation process. First section 32 is sized so that heavier components of the mixture can be separated from unreacted volatiles and fall toward second section 34. Third section 36 serves as a stripping section. Third section is sized so that an alcohol product 64 from the catalytic distillation process can be separated from a reaction mixture as a condensate and fall as a liquid 66 toward base 28.

Referring to FIG. 1, olefins feed system 14 feeds an olefin 44 to catalytic distillation column 12. Olefin 44 is fed under pressure in a direction indicated by arrows 46 via sequentially a first olefin feed line 48, and a second olefin feed line 52 through sidewalls 24 into interior cavity 30 of body 22 of catalytic distillation column 12 at a position closely below catalyst bed 40. Water feed system 16 includes a heat exchanger 60 whereby heat is recovered from liquids recovery system 18. Water 54 is fed under pressure in a direction indicated by arrows 56 via sequentially a first water feed line 58, heat exchanger 60, and a second water feed line 62 through sidewalls 24 into interior cavity 30 at a position closely above catalyst bed 40. Olefin 44 and water 54 react over catalyst 42 in catalyst bed 40 to produce a product mixture according to Equations 1 and 2. Referring to FIG. 2, the product mixture contains an alcohol 64 and an ether corresponding to olefin 44. Alcohol 64 separates from the reaction mixture as a liquid 66 and is collected at third portion 36 of interior cavity 30. A mixture comprising volatile components 68 of the reaction mixture separates from the reaction mixture and is collected at first portion 32 of interior cavity 30.

Figure 4:
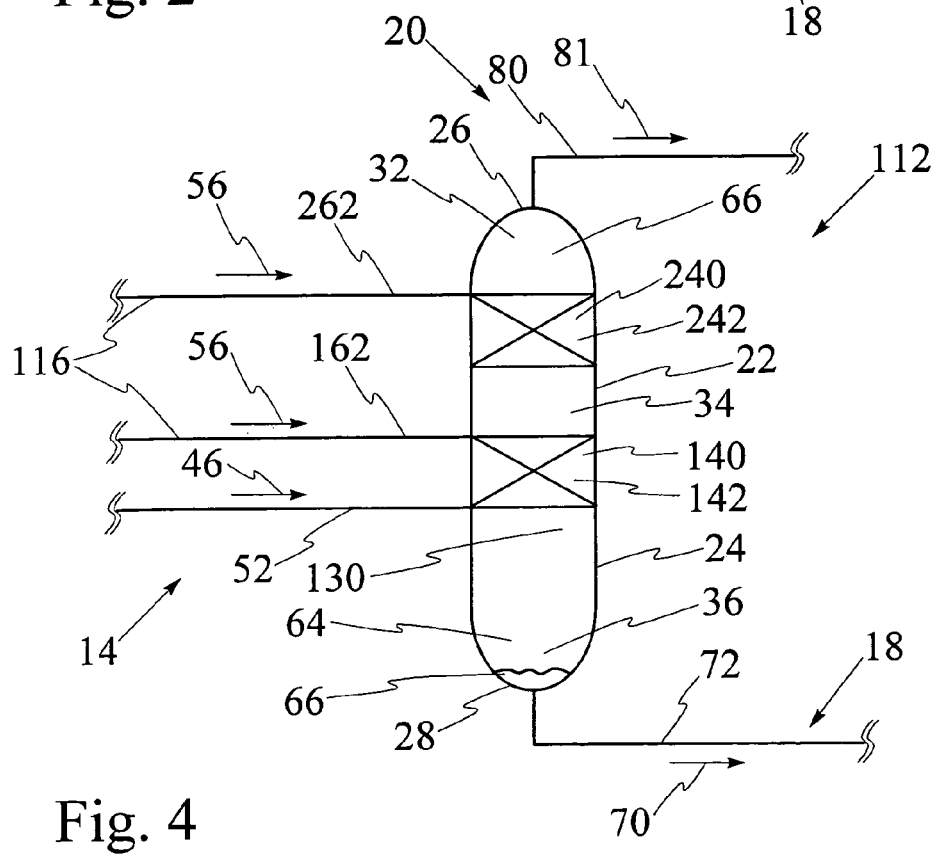
FIG. 4 is a schematic diagram of a catalytic distillation column having two catalyst beds for the catalytic distillation process shown in FIG. 3.
Figure 3:
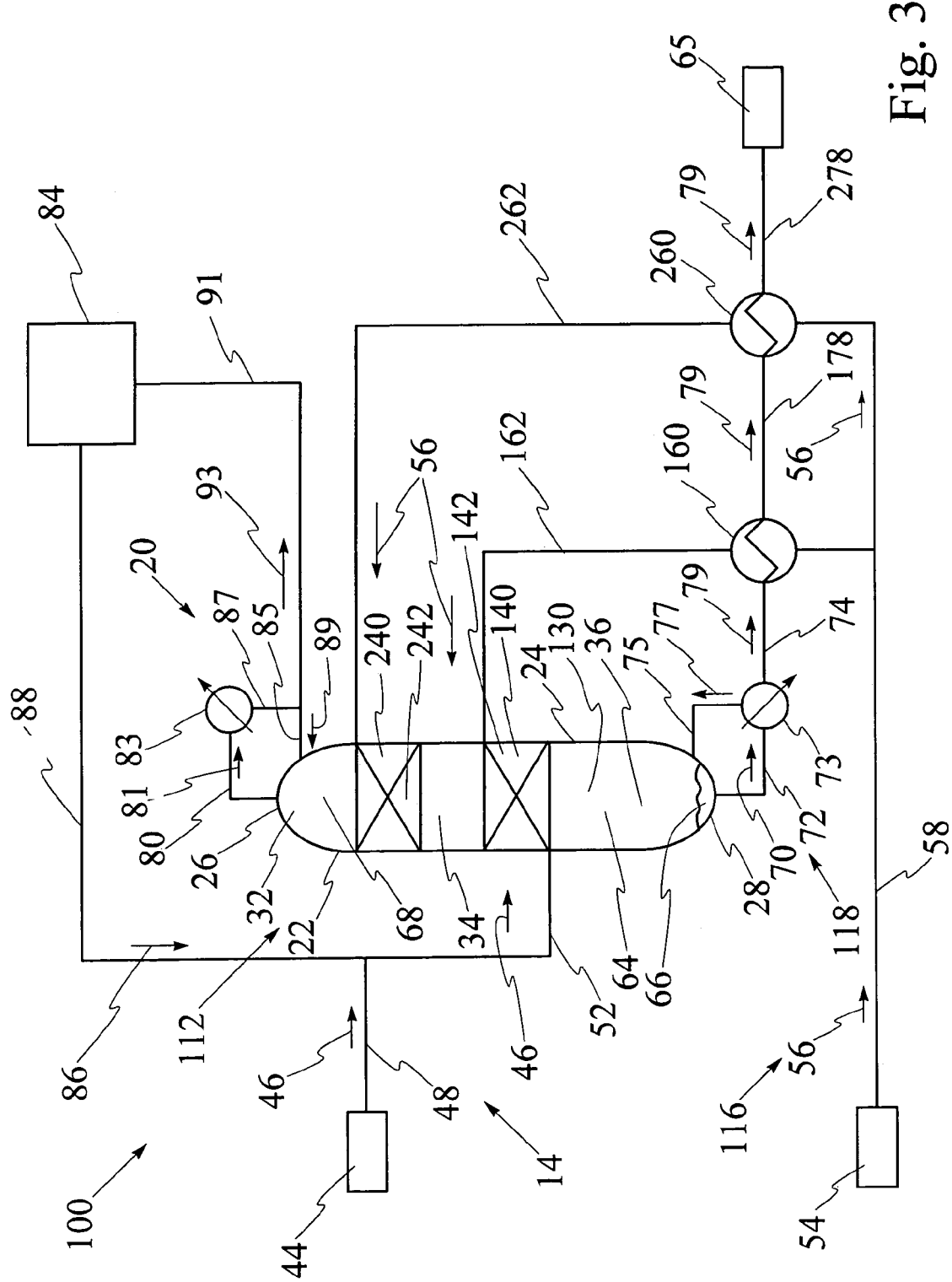
FIG. 3 is a schematic diagram of a catalytic distillation process for hydration of an olefin to the corresponding alcohol, in which the catalytic distillation column has two catalyst beds.
Figure 5:
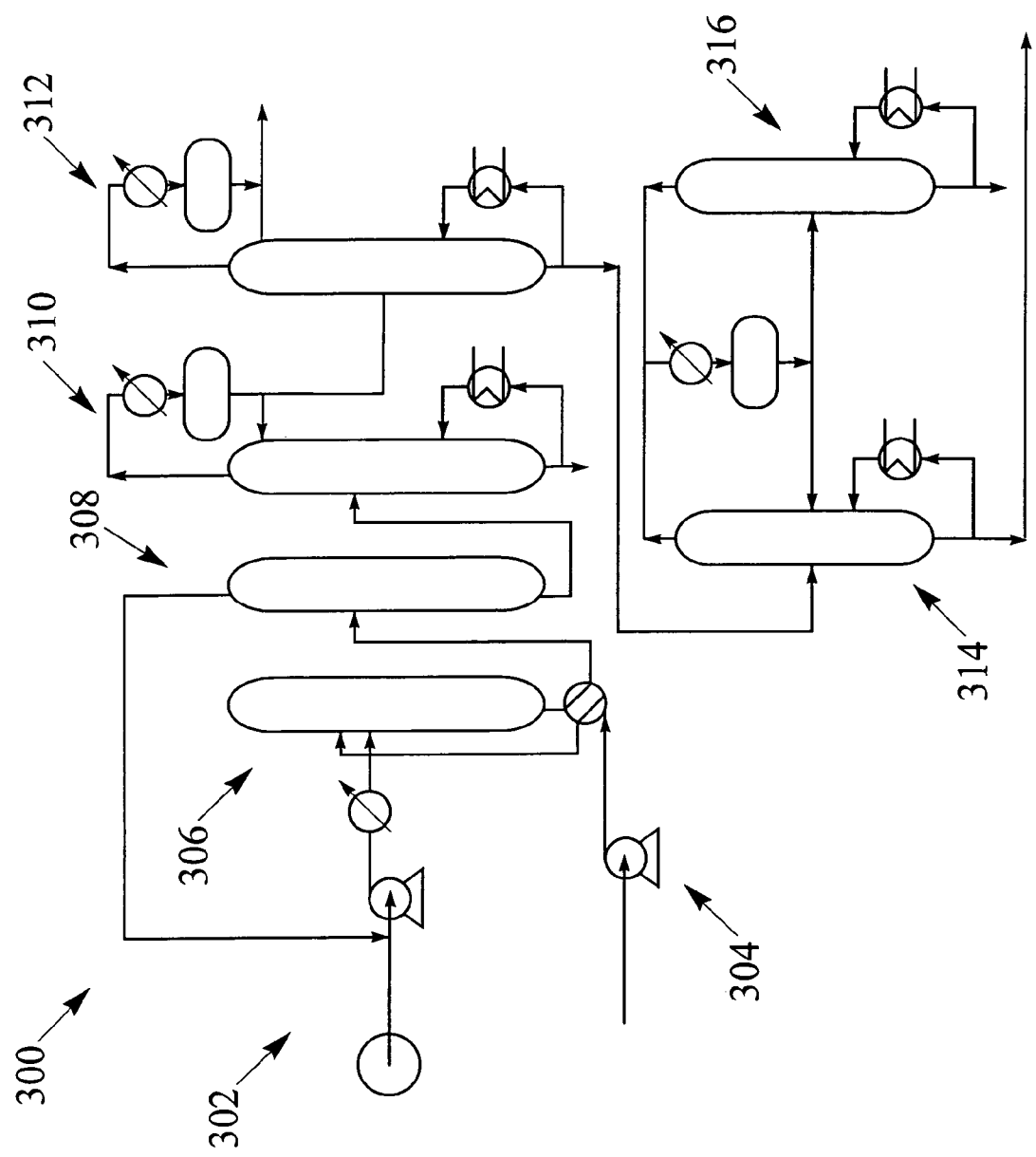
FIG. 5, labeled PRIOR ART, is a schematic diagram of the Tokyoyama process for hydration of propene to isopropanol, the process being an example of a conventional process for the production of an alcohol by hydration of an olefin.

Referring to FIGS. 3 and 4, second embodiment of equipment 100 includes a catalytic distillation column 112 having a first catalyst bed 140 and a second catalyst bed 240, first catalyst bed 140 and second catalyst bed 240 being spaced apart. Referring to FIG. 3, olefin 44 is fed into interior cavity 130 at a position closely below first catalyst bed 140. Water feed system 116 includes a first heat exchanger 160 and a second heat exchanger 260 whereby heat is recovered from liquid product recovery system 118. Water 54 is fed into interior cavity 130 via water feed lines 162 and 262 at positions closely above each of first catalyst bed 140 and second catalyst bed 240 respectively. First catalyst bed 140 contains a packed material comprising a first active olefin hydration catalyst 142 and second catalyst bed 240 contains a packed material comprising a second active olefin hydration catalyst 242. Second catalyst 242 optionally may be the same catalyst as first catalyst 142.

Catalyst bed 40, shown in FIG. 2, first catalyst bed 140 and second catalyst bed 240, shown in FIG. 4, are each in the form of a fixed bed. Catalyst 42, first catalyst 142 and second catalyst 242 each comprises a catalytic material having acidic properties. Conventional acidic catalysts active for hydration of an olefin to the corresponding alcohol are characteristically hydrophilic, and include: a cation exchange resin catalyst; a supported phosphoric acid catalyst; a catalyst comprising a heteropolyacid supported on a siliceous support; and a catalyst comprising a proton-exchanged form of a zeolite. In some embodiments, catalyst 42, first catalyst 142 and second catalyst 242 each are hydrophobic e.g. SILICALITE and sulfate-treated SILICALITE. SILICALITE is a trademark for a commercially available silica (Union Carbide Inc.) having a highly regular crystallographic structure, the structure being characterized by a large surface area, and interconnected cavities within the regular structure. The more hydrophobic catalyst has the advantage that water does not compete with an olefin for active catalyst sites as readily as for the catalyst sites of conventional hydrophilic catalysts. A consequence is that water has a lower propensity to block access by the olefin to the active catalyst sites of the more hydrophobic catalyst when compared with more hydrophilic catalysts. The rate of the olefin hydration reaction thereby is enhanced. It will be recognized that other hydrophobic catalysts can be used without departing from the spirit of the present invention. The acidity, and hence the activity, and the selectivity of the catalyst can be altered by depositing additional materials selected from olefin hydration catalysts and promoters on SILICALITE. The use of a more hydrophobic catalyst overcomes the limitation on reaction rate caused by the low solubility of olefins in water, without the need for intervention of a co-solvent as described by Marker et al. in U.S. Pat. No. 5,744,645.

Referring to FIGS. 1 through 4, liquid 66 rich in alcohol 64 is withdrawn from base 28 in a direction indicated by an arrow 70 via a first liquid product line 72. Referring to FIG. 1, liquid product recovery system 18 normally includes a reboiler 73 and a volatiles return line 75. Liquid 66 is heated in reboiler 73. A volatile fraction from heated liquid 66 is returned in a direction 77 from reboiler 73 through first return line 75 to third portion 36 of interior cavity 30. Substantially pure alcohol 65 is recovered as liquid product from reboiler 73 in a direction indicated by arrows 79 via sequentially a second liquid product line 74, heat exchanger 60, and a third liquid product line 78. Referring to FIG. 3, liquid product recovery system 118 also normally includes a reboiler 73 and a volatiles return line 75. Substantially pure alcohol 65 is recovered as liquid product from reboiler 73 in a direction indicated by arrows 79 via sequentially second liquid product line 74, first heat exchanger 160, a fourth liquid product line 178, second heat exchanger 260, and a fifth liquid product line 278.

Referring to FIGS. 1 through 4, a reaction mixture 68 comprising volatile components of the reaction mixture in catalytic distillation column 12 is withdrawn from top 24 of catalytic distillation column 12 via a volatiles line 80 in a direction indicated by an arrow 81. Referring to FIGS. 1 and 3, volatiles recovery system 20 normally includes a condenser 83 and a liquids return line 85. Reaction mixture 68 is condensed in condenser 83 to volatile liquids 87. A first portion of volatile liquids 87 is returned in a direction indicated by an arrow 89 to first portion 32 of interior cavity 30 through liquids return line 85. A second portion of volatile liquids 87 is recovered via volatile liquids recovery line 91 in a direction indicated by an arrow 93.

Volatile liquids 87 are rich in olefin 44. Second portion of volatile liquids 87 is optionally directed to an olefin recovery plant 84 where the stream is separated into an olefin-rich fraction and an alkane-rich fraction. The olefin-rich fraction is recycled to catalytic distillation column 12 in a direction indicated by arrow 86 via olefin recycle line 88 and second olefin feed line 52.

The present invention confers advantages over the PRIOR ART, as will now be shown through the example of hydration of propene to isopropanol. Hydration of propene to isopropanol using existing technology is accomplished by one of several different processes. The performance of these processes is characterized as presented in TABLE 1. In TABLE 1 data are listed under headings A through E for the following PRIOR ART processes and under F for the process of the present invention: A: indirect hydration in one step; B: indirect hydration in two steps; C: fixed bed vapor phase direct hydration; D: trickle bed mixed phase direct hydration (Deutsche Texaco AG, as described in *Hydrocarbon Processing*, November 1972, pages 113–116); E: liquid phase direct hydration (Tokyoyama Soda Co., Ltd.) illustrated in FIG. 5; F: catalytic distillation according to the present invention using second embodiment of equipment 100 illustrated in FIG. 3.

Referring to TABLE 1, liquid 66 is richer in alcohol 64 when compared with a liquid product from a conventional process for production of the alcohol by hydration of the olefin.

Referring to FIG. 5, an example of the PRIOR ART is a process 300 operated by the Tokyoyama company for the production of isopropanol. In common with the process of the present invention, PRIOR ART process 300 has a propene feed system 302, a water feed system 304 and a reactor 306. The product is an aqueous mixture from which isopropanol is to be recovered. The product mixture from reactor 306 is fed sequentially to a separator 308, an azeo column 310, a light end recovery column 312, a dehydration column 314, and an isopropanol recovery column 316, each of which is supported by appropriate valves and pressure and temperature controllers. A comparison of FIG. 5 with FIGS. 1 and 3 shows the greater complexity and consequent capital costs of PRIOR ART process 300 when compared with the present invention.

According to the second aspect of the present invention an olefin and an azeotropic mixture comprising the first alcohol and water are continuously fed to a catalytic distillation column. A hydration reaction is performed between the water in the azeotropic misture and an added olefin. The hydration reaction is performed at a temperature and a pressure selected so that: the rate of the hydration reaction is high; conversion of the olefin to the corresponding second alcohol is favored over conversion to the corresponding ether, and etherification of the olefin does not occur to a measurable degree; the olefin is largely in the vapour phase; and a liquid product mixture comprising the first alcohol and the second alcohol is produced. The first alcohol and the second alcohol are continuously removed as a liquid product stream from the base of the catalytic distillation column. These operating conditions provide for an alcohol content of the liquid product stream of over 99%.

A typical temperature range is 70–180° C.

A typical pressure range is 0.25–2.5 MPa.

A first embodiment of the equipment and an advantageous method for the simultaneous hydration of an olefin to a corresponding secondary alcohol and recovery of the alcohol will now be described with reference to FIGS. 14 through 17. A second embodiment of the equipment will be described with reference to FIG. 18. The invention will then be illustrated using non-limiting examples to illustrate procedures and conditions applicable to recovery of substantially anhydrous ethanol, with reference to FIGS. 14 through 18.

A first embodiment of equipment 410 for said method for hydration of an olefin to the corresponding alcohol will be described with reference to FIGS. 14 and 15. A second embodiment of equipment 500 will be described with reference to FIG. 18. One PRIOR ART process for the hydration of an olefin to the corresponding alcohol is illustrated in FIG. 5, for purpose of comparison of a conventional method for recovery of a substantially anhydrous alcohol with the method of the present invention.

Figure 14:
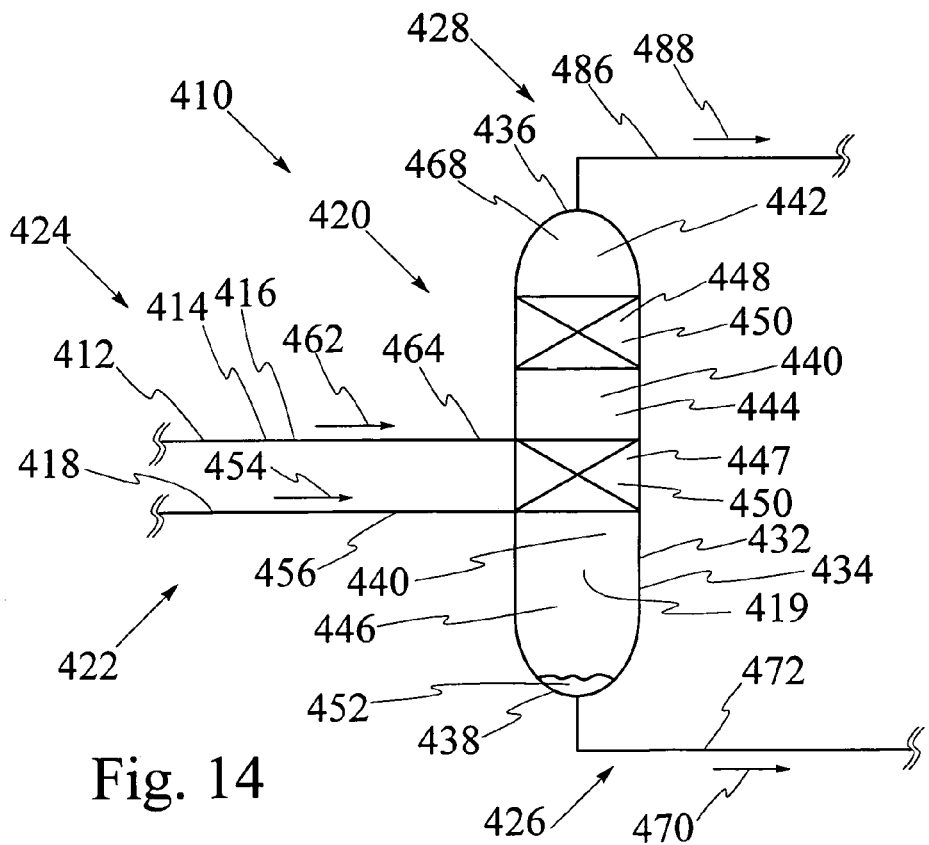
FIG. 14 is a schematic diagram of a catalytic distillation column for recovery of a first alcohol in a substantially anhydrous state from an azeotropic mixture containing both of the first alcohol and water, in which the catalytic distillation column has two catalyst beds.
Figure 15:
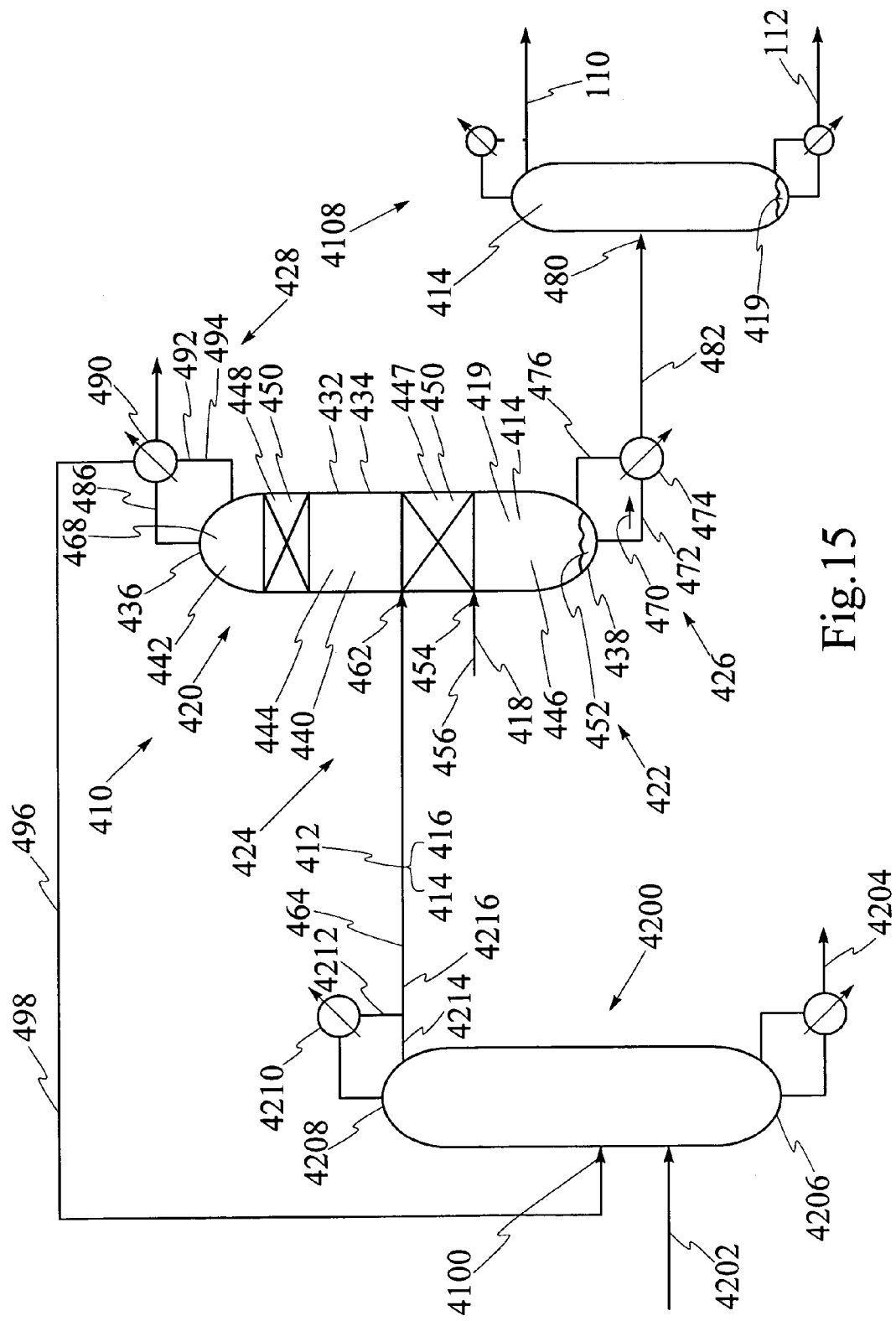
FIG. 15 is a schematic diagram of a catalytic distillation process for the recovery of substantially anhydrous ethanol from the product stream from a distillation process for the production of an azeotropic mixture of ethanol and water, including the catalytic distillation shown in FIG. 14.

Referring to FIGS. 14 and 15, first embodiment of equipment 410 for continuous and simultaneous removal of the water content of azeotropic mixture 412 containing first alcohol 414 and water 416 by hydration of an olefin 418 to a second alcohol 419 includes a catalytic distillation column 420, an olefin feed system 422, an azeotropic mixture feed system 424, a liquid product recovery system 426, and a volatiles recovery system 428.

Referring to FIG. 14, catalytic distillation column 420 has a body 432 having elongate cylindrical sidewalls 434, a top 436 and a base 438 defining an interior cavity 440. Body 432 is constructed of a material that is unaffected by the components of a reaction mixture contained within interior cavity 440. Body 432 can be insulated so as to maintain and withstand a temperature at which a reaction is conducted within interior cavity 440. Body 432 is capable of containing a pressurized reaction mixture at a pressure at which the reaction is conducted. Interior cavity 440 has a first portion 442, a second portion 444, and a third portion 446. Second portion 444 serves as a reaction zone during a catalytic distillation process. At least two catalyst beds 447, 448 that are in a vertically spaced-apart relationship are situated within second portion 444. Catalyst beds 447, 448 contain packed material comprising an active olefin hydration catalyst 450. Water 416 and olefin 418 react over catalyst 450 to produce second alcohol 419. Rectification of the volatile components of the reaction mixture occurs in first portion 442 during the catalytic distillation process. First section 442 is sized so that heavier components of the mixture can be separated from unreacted volatiles and fall toward second section 444. Third section 446 serves as a stripping section. Third section is sized so that ethanol 414 and second alcohol 419 can be separated from a reaction mixture as a condensate and fall as liquid 452 toward base 438.

Olefin feed system 422 feeds olefin 418 to catalytic distillation column 412. Olefin 418 is fed under pressure in a direction indicated by arrow 454 via an olefin feed line 456 through sidewalls 434 into interior cavity 440 of body 432 of catalytic distillation column 412 at a position closely below the lower catalyst bed 447. Optionally, azeotropic mixture feed system 424 includes a heat exchanger (not illustrated) whereby heat is recovered from liquids recovery system 426. Azeotropic mixture 412 is fed under pressure in a direction indicated by arrow 462 via sequentially an azeotropic mixture feed line 464 through sidewalls 434 into interior cavity 440 at a position closely above the lower catalyst bed 447. Olefin 418 and water 416 from azeotropic mixture 412 react over catalyst 450 in catalyst beds 447, 448 to produce a product mixture containing both first alcohol 414 and second alcohol 419.

Referring to FIG. 15, for purposes of example only, azeotropic mixture 412 can be the product from a distillation tower 4200 for separation of azeotropic mixture 412 from an aqueous alcohol stream 4202. A water stream 4204 is separated as liquid at a bottom 4206 of tower 4200 from aqueous alcohol stream 4202. Azeotropic mixture 412 is recovered as vapour at a top 4208 of tower 4200. Said vapour is condensed in a condenser 4210 to form a liquid stream 4212. Liquid stream 4212 is divided into a first fraction 4214 that is returned to tower 4200 and a second fraction 4216 that is azeotropic mixture 412 fed to column 420. For example, when alcohol 414 is ethanol, industrial processes including fermentation can produce an aqueous solution containing approximately 10% ethanol. Said aqueous solution is separated by distillation in tower 4200 into water stream 4204 and a near azeotropic mixture comprising approximately 90% ethanol and 10% water.

Referring to FIGS. 14 and 15, first alcohol 414 and second alcohol 419 separate from the reaction mixture as liquid 452 and are collected at third portion 446 of interior cavity 440. A mixture comprising volatile components 468 of the reaction mixture separates from the reaction mixture and is collected at first portion 442 of interior cavity 440.

Catalyst beds 447, 448, shown in FIG. 15, are fixed beds. Catalyst 450 comprises a catalytic material having acidic properties. Conventional acidic catalysts active for hydration of an olefin to the corresponding alcohol include: a cation exchanged resin catalyst as described by Gonzalez et al. and by Bezman; a supported phosphoric acid catalyst as described by Hoecker et al.; a catalyst comprising a heteropolyacid supported on a siliceous support as described by Haining et al.; and a catalyst comprising a proton-exchanged form of a zeolite as described by Wang et al. Preferably, catalyst 450 is more hydrophobic than a conventional olefin hydration catalyst. An example of a suitable hydrophobic olefin hydration catalyst is SILICALITE. SILICALITE is a trademark for a commercially available silica (Union Carbide Inc.) having a highly regular crystallographic structure, the structure being characterized by a large surface area, and interconnected cavities within the regular structure. We have also found that the catalytic activity increased significantly when the SILICALITE is sulfated e.g. with 1 N sulfuric acid. This results in a sulfated SILICALITE material. These catalysts confer advantages over conventional olefin hydration catalysts, as will now be described. The SILICALITE olefin hydration catalyst is more hydrophobic than conventional olefin hydration catalysts. The more hydrophobic catalyst has the advantage that water does not compete with an olefin for active catalyst sites as readily as for the catalyst sites of conventional catalysts. A consequence is that water has a lower propensity to block access by the olefin to the active catalyst sites of the more hydrophobic catalyst when compared with more hydrophilic catalysts. The rate of the olefin hydration reaction thereby is enhanced. It will be recognized that other similar hydrophobic olefin hydration catalysts can also be employed without departing from the spirit of the present invention. The acidity, and hence the activity, and the selectivity of the catalyst can be altered by depositing additional materials selected from olefin hydration catalysts and promoters on SILICALITE. The use of a more hydrophobic catalyst overcomes the limitation on reaction rate caused by the low solubility of olefins in a liquid azeotropic mixture, without the need for intervention of a co-solvent as described by Marker et al.

Referring to FIGS. 14 and 15, liquid 452 rich in first alcohol 414 and second alcohol 419 is withdrawn from base 438 in a direction indicated by an arrow 470 via a first liquid product line 472. Referring to FIG. 15, liquid product recovery system 426 normally includes a reboiler 474 and a volatiles return line 476. Liquid 452 is heated in reboiler 474. A volatile fraction from heated liquid 452 is returned from reboiler 474 through first return line 476 to third portion 446 of interior cavity 440. A substantially anhydrous mixture of first alcohol 414 and second alcohol 419 is recovered as liquid product from reboiler 474 in a direction indicated by arrows 480 via sequentially a second liquid product line 482.

Referring to FIG. 14, a reaction mixture 468 comprising volatile components of the reaction mixture in catalytic distillation column 420 is withdrawn from top 436 of catalytic distillation column 412 via a volatiles line 486 in a direction indicated by an arrow 488. Referring to FIG. 15, volatiles recovery system 428 normally includes a condenser 490 and a liquids return line 492. Reaction mixture 468 is rich in unreacted olefin 418, and also contains a substantial amount of alcohol 414. Reaction mixture 468 is partly condensed in condenser 490 to volatile liquids. A first fraction 494 of reaction mixture 468 that is rich in unreacted olefin 418 and alcohol 414 is returned to first portion 432 of interior cavity 440 through liquids return line 492. A second fraction 496 of reaction mixture 468 that is rich in alcohol 414 is recovered via volatiles recovery line 498 in a direction indicated by an arrow 4100, and returned to tower 4200 for recovery of alcohol 414.

A distillation process can separate first alcohol 414 and second alcohol 419 to the corresponding substantially pure (anhydrous) products, as illustrated in FIG. 15. Liquid product 452 is fed in direction 480 to an alcohol distillation column 4108. When the process of the present invention is used to dehydrate a light first alcohol 414, and olefin 418 is hydrated to form a heavier (higher molecular weight) second alcohol 419, first alcohol 414 is recovered as a volatile fraction 4110 and second alcohol 419 is recovered as a bottom fraction 4112. When first alcohol 414 is ethanol, and it is desired that said ethanol is to be separated from second alcohol 419 by distillation, it is necessary that olefin 418 has at least five carbon atoms. When olefin 418 is 2-methyl-2-butene, second alcohol 419 is 2-methyl-2-butanol. It is found that liquid product 452 contains no detectable amounts of ethyl (2-methyl-2-butyl) ether, which is consistent with the findings of the Linnekoski et al. reference. The boiling points of ethanol (78° C. at atmospheric pressure) and 2-methyl-2-butanol (102° C. at atmospheric pressure) are sufficiently far apart so as to allow separation by distillation in column 4108.

Alternatively, olefin 418 can be selected so that first alcohol 414 and second alcohol 419 form a close boiling mixture point that is useful, for example as an additive for liquid automotive fuels. An example of a close boiling mixture is ethanol and 2-methyl-2-propanol (boiling point 82.5° C. at atmospheric pressure). The characteristics of a process by which amyl alcohol has been produced by reactive distillation over AMBERLIST 15 catalyst have been studied by Gonzalez et al. (Industrial and Engineering Chemistry Research, 1997, 36, 3845–3853).

Figure 18:
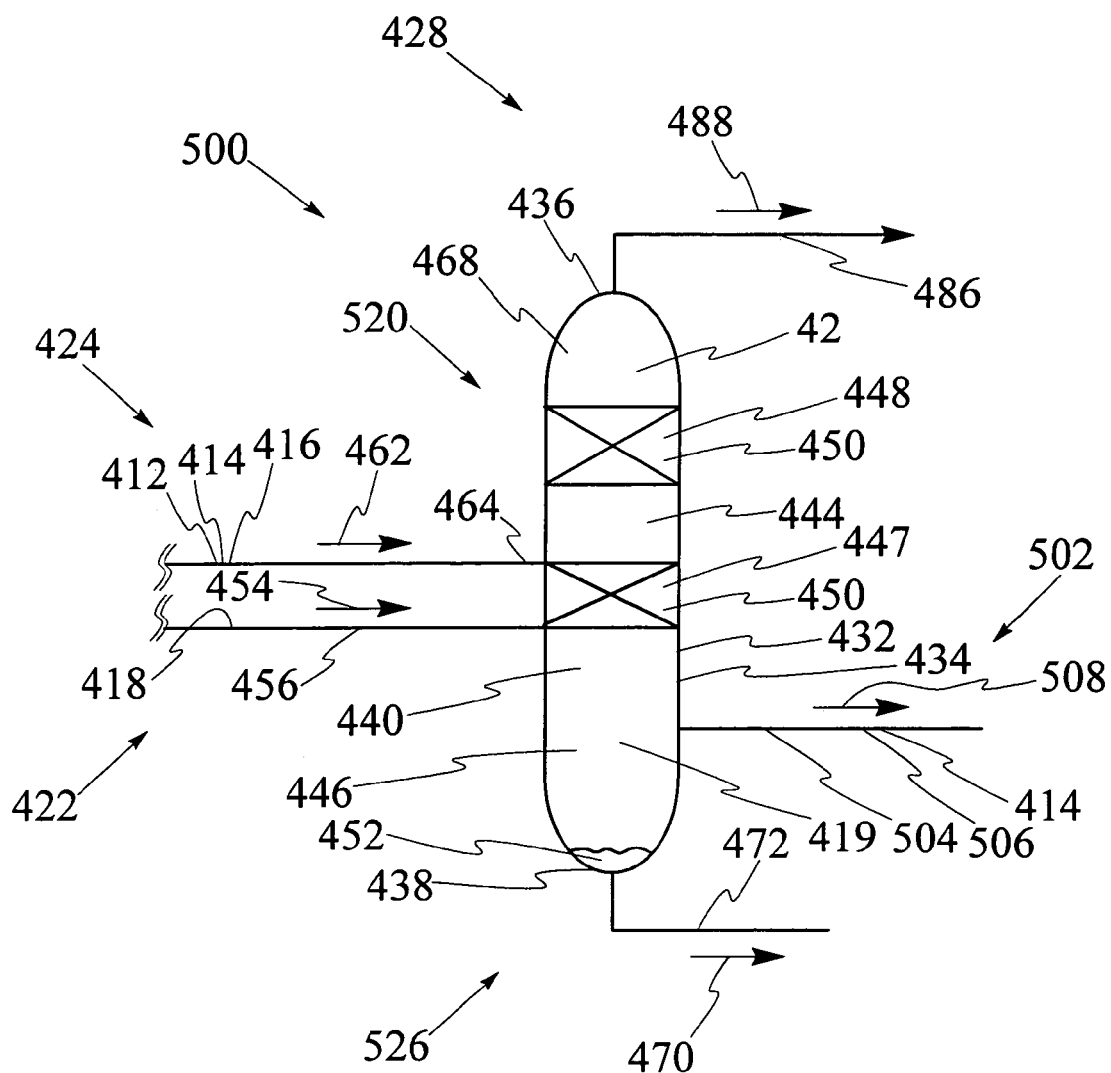
FIG. 18 is a schematic diagram of a catalytic distillation column for recovery of a first alcohol in a substantially anhydrous state from an azeotropic mixture containing both of the first alcohol and water shown in FIG. 14, in which a take off line for a side stream is fitted at the side of the column as a second system for recovery of liquid product.

Referring to FIG. 18, second embodiment of equipment 500 is similar to first embodiment of equipment 410, with the difference that second embodiment of equipment 500 includes both of a first liquid product recovery system 526 that is substantially similar to liquid product recovery system 426 of first embodiment of equipment 410 and a second to isopropanol using existing technology is accomplished by one of several different processes, as described above. In each conventional process, the isopropanol produced in the reactor is one component in a mixture with water and other products. Water is removed from the isopropanol product mixture using countercurrent or extractive methods. The isopropanol must then be recovered from the fluid of the countercurrent stream or from the extraction fluid, frequently requiring several expensive steps. The present invention removes the water by hydration of an olefin to directly form a second alcohol that is a valuable and easily separable product. Referring to FIG. 5, an example of the PRIOR ART is a process 300 operated by the Tokyoyama company for the production of isopropanol. Process 300 has a propene feed system 302, a water feed system 304 and a reactor 306. The product is an aqueous mixture from which isopropanol is to be recovered. The product mixture from reactor 306 is fed sequentially to a separator 308, an azeo column 310, a light end recovery column 312, a dehydration column 314, and an isopropanol recovery column 316, each of which is supported by appropriate valves and pressure and temperature controllers. A comparison of FIG. 5 with FIG. 15 shows the greater complexity and consequently the higher capital costs of PRIOR ART process 300 when compared with the present invention. It will be recognized that substituting column 520 of second embodiment of equipment 500 for column 20 of first embodiment of equipment 410 will also confer advantages of the present invention over the PRIOR ART.

TABLE 1

Comparison of the present invention with conventional catalytic distillation processes. (n/a means data is proprietary or otherwise not available)

| | Process: | | | | | |
|---|---|---|---|---|---|---|
| | A | B | C | D | E | F |
| Concentration of propene in feed stream (wt %): | 40–60 | 40–60 | 99 | 92 | 95 | 95 |
| Catalyst: | sulfuric acid (>80%) | sulphuric acid (60–80%) | $WO_3$—$ZnO/H_3PO_4$ on $SiO_2$ | Sulphonic acid ion-exchange resin | acidic aqueous solution of silicotungstate | strong acid supported on inorganic support |
| Catalyst regeneration and recycle needed?: | Yes | Yes | n/a | n/a | Yes | No |
| Operating pressure (MPa): | 1–1.2 | 2.5 | 2.5–6.6 | 8–10 | 20.3 | 1.5–4.0 |
| Operating temperature (° C.): | 20–30 | 60–65 | 240–260 | 130–160 | 270 | 50–225 |
| Feed ratio ($H_2O/C_3H_6$): | n/a | n/a | 1:4–1:10 | 12:1–15:1 | n/a | 1:3–1:5 |
| Conversion of propene (%): | >93 | >93 | 5–6 | >75 | 60–70 | 20–33 |
| Selectivity to isopropanol (%): | 98 | 98 | 96 | 93 | 98–99 | >99.8 | liquid product recovery system 502. Second embodiment of equipment 500 includes a catalytic distillation column 520, olefin feed system 422, azeotropic mixture feed system 424, a liquid product recovery system 426, and a volatiles recovery system 428. Second liquid product recovery system 502 comprises a take off line 504 for a side stream. Take off line 504 extends from third portion 446 of interior 440 of column 520 at a position adjacent a distillation tray (not illustrated) situated between base 438 and lower catalyst bed 447. A liquid mixture 506 rich in ethanol 414 can be withdrawn as a side stream in a direction indicated by an arrow 508 from interior 440 through take off line 504.

The present invention confers advantages over the PRIOR ART, as will now be shown through the example of production and recovery of isopropanol. Hydration of propene The process of the first aspect of the present invention will now be illustrated using the following non-limiting examples. In each EXAMPLE, the process described and the data obtained have been modeled using the commercially available computer program ASPENPLUS, with MESH equations and the UNIFAC method. The results have been confirmed by experiment using at least one of the AMBERLIST series of acidic cation exchanged resins or SILICALITE as catalyst 42 in laboratory scale equipment for first embodiment of equipment 10, and as both of first catalyst 142 and second catalyst 242 in laboratory scale equipment for second embodiment of equipment 100.

EXAMPLES

Examples 1 through 4 will describe the catalytic distillation process of the present invention as applied to the hydration of propene for the production of substantially anhydrous isopropanol, using a range of operating conditions. Example 5 will describe a similar process for the production of substantially anhydrous tertiary butanol by the hydration of isobutene.

In each of the Examples the positions within the pertinent catalytic distillation column will be identified as numbered stages. Stage 1 is a distillation stage immediately below top 26. Further stages are then numbered sequentially in a direction toward base 28.

Example 1

Figure 9:
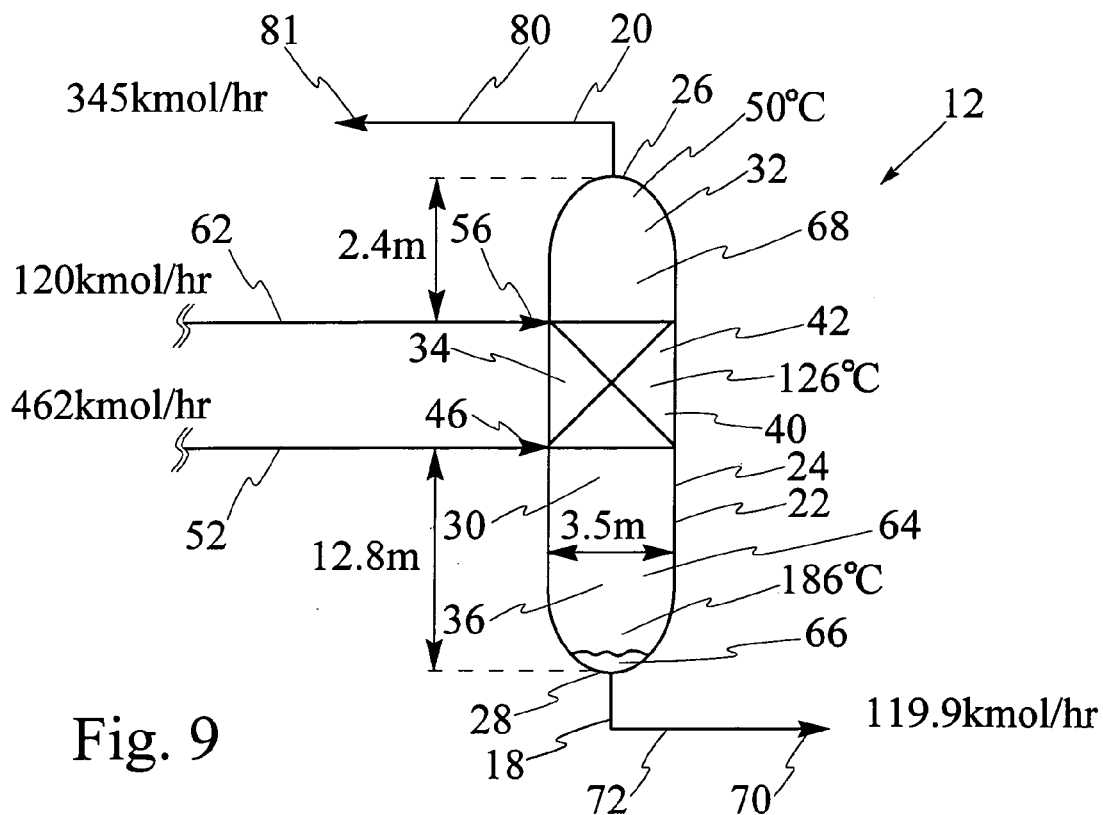
FIG. 9 is a schematic diagram showing the dimensions of the catalytic distillation column having one catalyst bed shown in FIG. 2, the temperatures at three positions, and the flow rates of the feed and exit streams for hydration of propene to isopropanol at a pressure of 2 megaPascals.

Referring to FIG. 9, catalytic distillation column 12 having single catalyst bed 40 has been used for hydration of propene to isopropanol at a pressure of 2 megaPascals. The reaction mixture includes propene, water, isopropanol and di-isopropyl ether, also known as DIPE. The computer model was run for catalytic distillation column having the dimensions illustrated in FIG. 9. It has been found that catalytic distillation column 12 having the above dimensions is effective for separation of propene at top 26 and liquid isopropanol at base 28. First portion 32 of interior cavity 30 has four stages for rectification of volatiles. Stage 5 comprises a second portion 34 of interior cavity 30 and contains catalyst bed 40. Third portion 36 of interior cavity 30 comprises stage 6 through stage 26, for stripping liquid isopropanol from the reaction mixture. The temperatures at stage 1, stage 26, and at catalyst bed 40 at stage 5 respectively are 50° C., 186° C. and 126° C., as illustrated. The molar feed rates for propene and water and the recovery rates for propene and isopropanol are each illustrated as values in kilomoles per hour. Propene conversion is 25% and water conversion is in excess of 99%. The purity of the isopropanol product stream is over 99% under these operating conditions, with the balance being mainly water and a trace of DIPE.

Example 2

Figure 10:
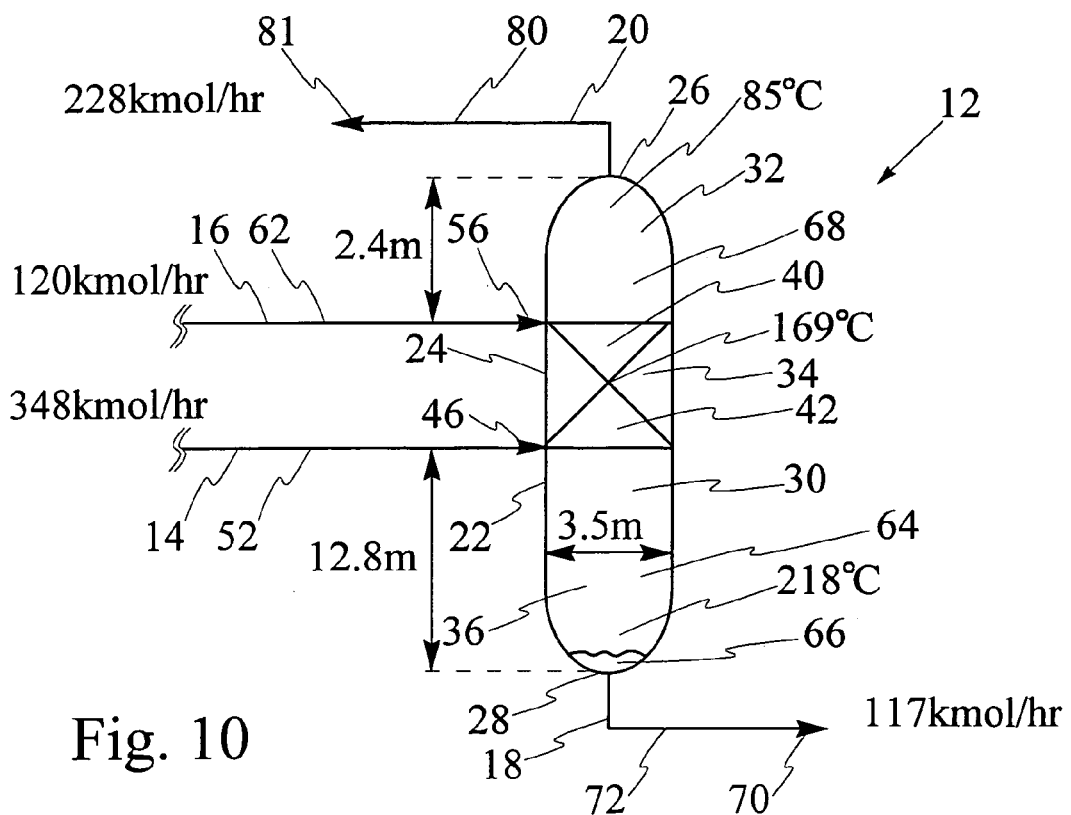
FIG. 10 is a schematic diagram showing the dimensions of the catalytic distillation column having one catalyst bed shown in FIG. 2, the temperatures at three positions, and the flow rates of the feed and exit streams for hydration of propene to isopropanol at a pressure of 4 megaPascals.

Referring to FIG. 10, catalytic distillation column 12 having substantially the same design and size as in Example 1 has been used for hydration of propene to isopropanol at a pressure of 4 megaPascals. The computer model has been used to determine that the temperatures at stage 1, stage 26, and at catalyst bed 40 at stage 5 respectively are 85° C., 218° C. and 169.6° C., as illustrated in FIG. 10. The molar feed rates for propene and water and the recovery rates for propene and isopropanol are each illustrated as values in kilomoles per hour. Propene conversion is 35%, water conversion is 96.7%, and the purity of the isopropanol stream is over 95%, with 5% DIPE, under these operating conditions.

Example 3

Figure 11:
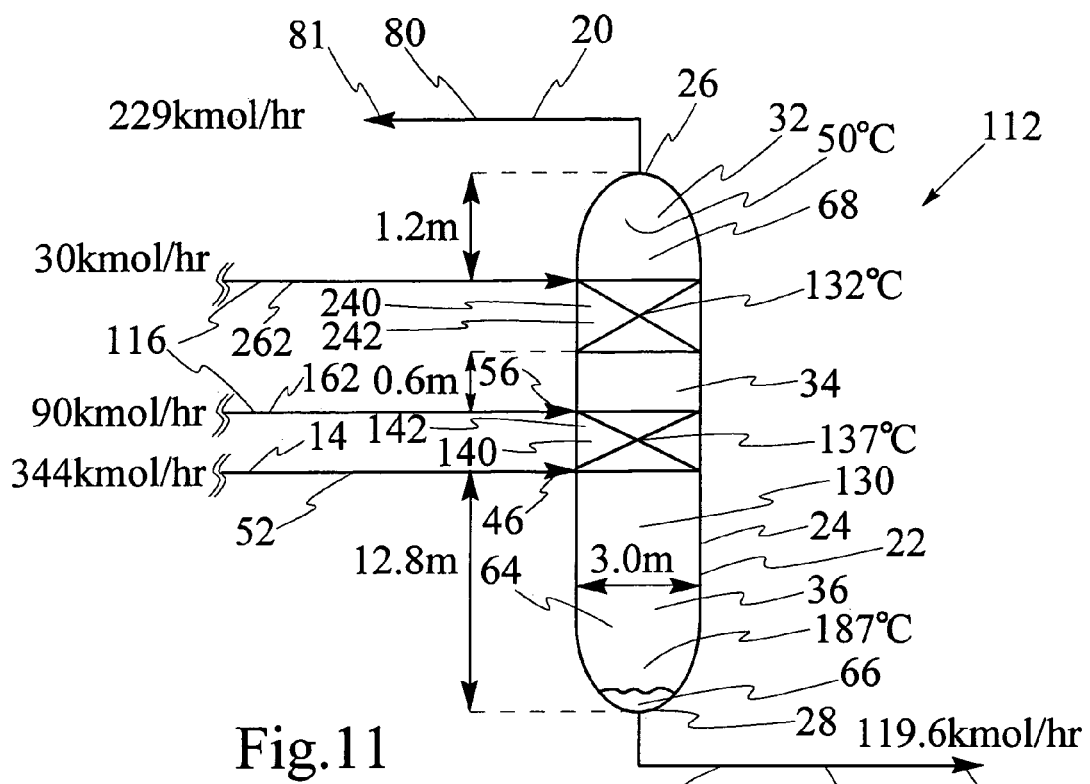
FIG. 11 is a schematic diagram showing the dimensions of the catalytic distillation column having two catalyst beds shown in FIG. 4, the temperatures at four positions, and the flow rates of the feed and exit streams for hydration of propene to isopropanol at a pressure of 2 megaPascals.

Referring to FIG. 11, catalytic distillation column 112 having two spaced apart catalyst beds 140 and 240 has been used for hydration of propene to isopropanol at a pressure of 2 megaPascals. The computer model was run for catalytic distillation column having the dimensions illustrated in FIG. 11. First portion 32 of interior cavity has two stages for rectification of volatiles. Second portion 34 contains first catalyst bed 140 at stage 5 and second catalyst bed 240 at stage 3, first catalyst bed 140 and second catalyst bed 240 being spaced apart by stage 4. Third portion 36 comprises stage 6 through stage 26, for stripping liquid isopropanol from the reaction mixture. The temperatures at stage 1, stage 28, at first catalyst bed at stage 5 and at second catalyst bed at stage 3 respectively are 50° C., 187° C., 137° C. and 132° C., as illustrated. The molar feed rates for propene and water and the recovery rates for propene and isopropanol are each illustrated as values in kilomoles per hour. Propene conversion is 35% and water conversion is in excess of 99%. The purity of the isopropanol stream is over 99% under these operating conditions, with the balance being mainly water and a trace of DIPE.

Figure 6:
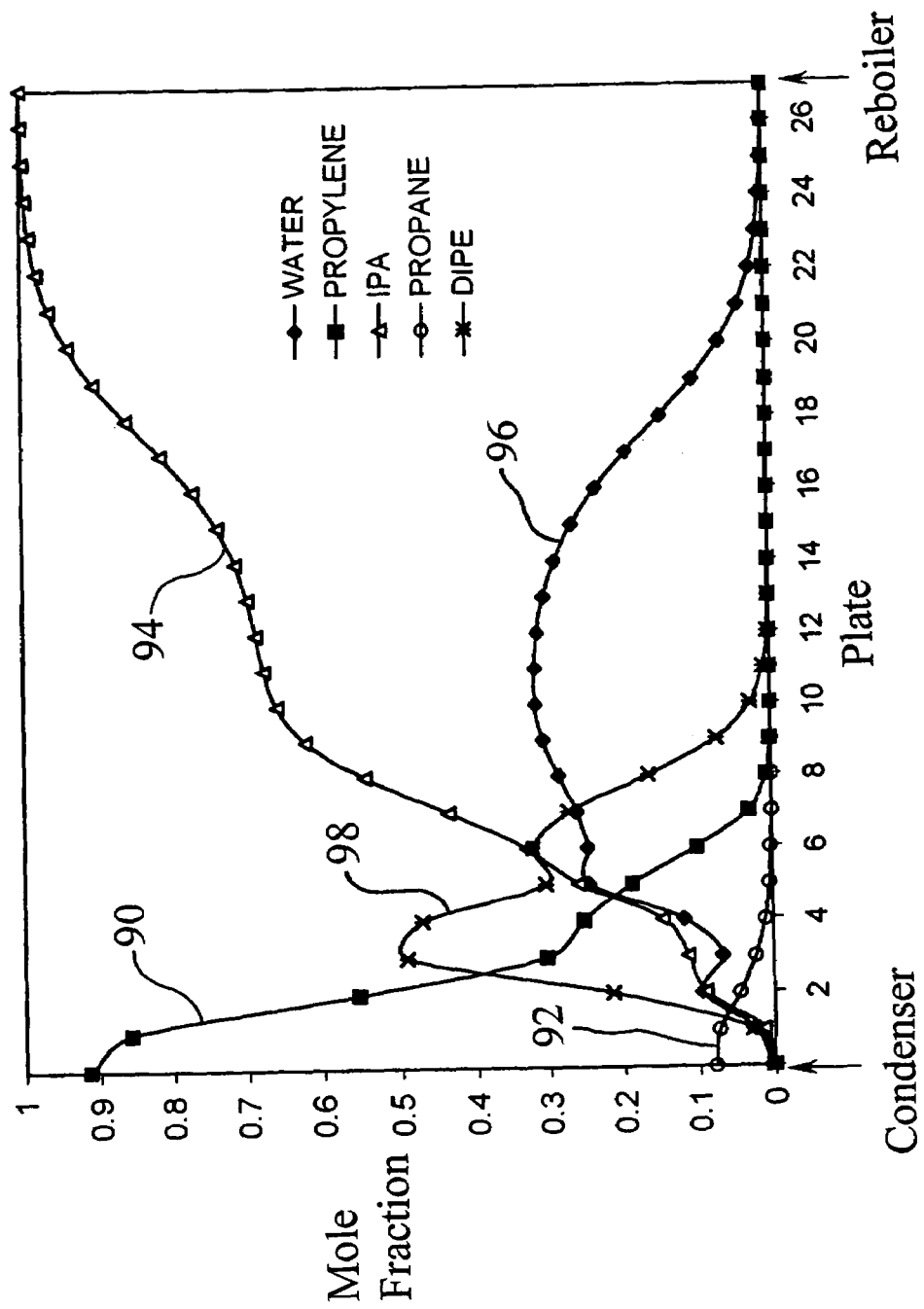
FIG. 6 is a profile of the steady state composition of the components of the reaction mixture during hydration of propene to isopropanol at an operating pressure of 2 megaPascals in the catalytic distillation column having two catalyst beds shown in FIG. 4.

The profile of the reaction mixture by stages is illustrated in FIG. 6 for use of catalytic distillation column 112, and condenser 73 and reboiler 83, as illustrated in FIG. 3. The effluent stream fed to reboiler 83 and to first volatiles line 80 comprises only unreacted propene, the mole fraction of which is shown as plot line 90 in FIG. 6, and propane, shown as plot line 92, a contaminant in propene feed 44. Liquid product 66 collected via first product line 72 comprises over 99% isopropanol, shown as plot line 94, containing a very small amount of water, shown as plot line 96, and DIPE, shown as plot line 98. At stage 12 through stage 26 of the liquid product stripping zone at third portion 36 of interior cavity 30, substantially all water is volatilized as a volatile two-component azeotropic mixture with isopropanol. At stage 6 through stage 12 a volatile three-component mixture of water, DIPE and isopropanol is returned to the vicinity of reaction zone at second portion 34. In the rectification zone at first portion 32, substantially all isopropanol, water and DIPE are returned as heavier components from stage 1 and stage 2 into the reaction zone at second portion 34.

Example 4

Figure 12:
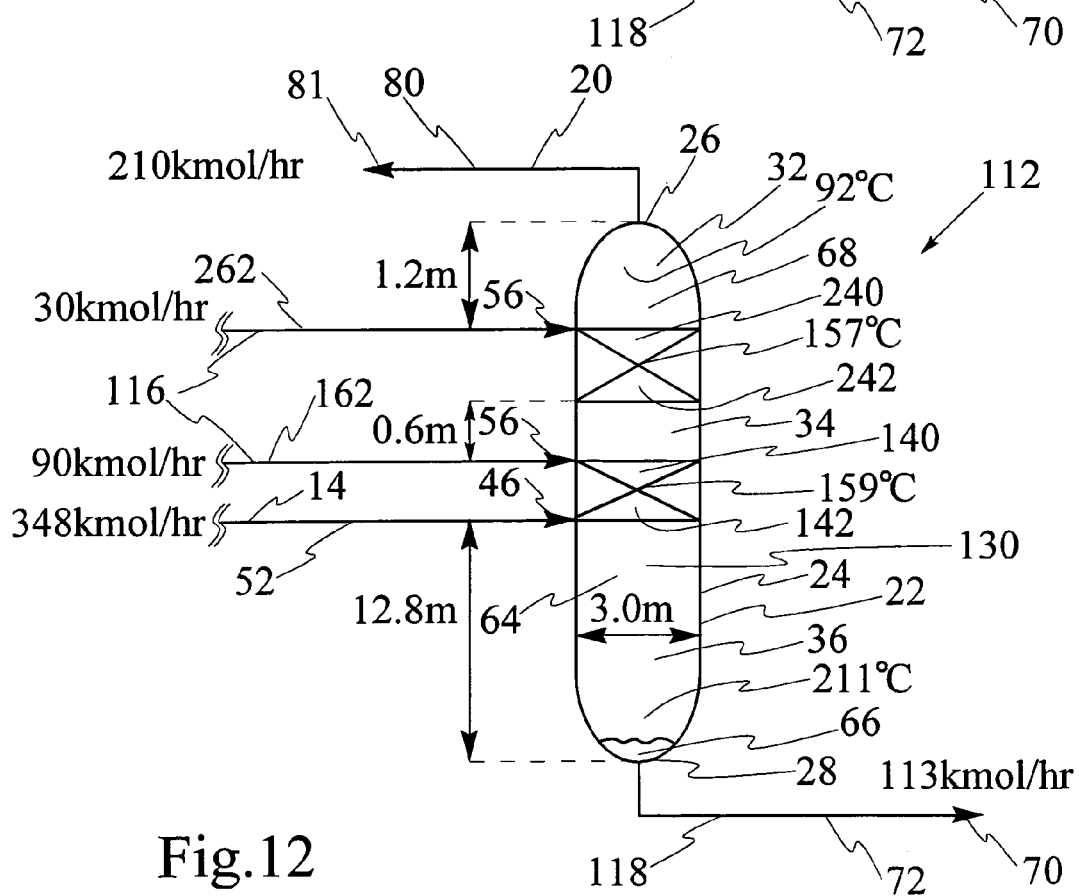
FIG. 12 is a schematic diagram showing the dimensions of the catalytic distillation column having two catalyst beds shown in FIG. 4, the temperatures at four positions, and the flow rates of the feed and exit streams for hydration of propene to isopropanol at a pressure of 4 megaPascals.

Referring to FIG. 12, catalytic distillation column 112 having substantially the same design and size as in Example 3 has been used for hydration of propene to isopropanol at a pressure of 4 megaPascals. The computer model has been used to determine that the temperatures at stage 1, stage 28, at first catalyst bed at stage 5 and at second catalyst bed at stage 3 are respectively 92° C., 211° C., 159° C. and 157° C., as illustrated. The molar feed rates for propene and water and the recovery rates for propene and isopropanol are each illustrated as values in kilomoles per hour. Propene conversion is 36% and water conversion is in excess of 99%. The purity of the isopropanol stream is over 99% under these operating conditions, with the balance being mainly water and a trace of DIPE.

Figure 7:
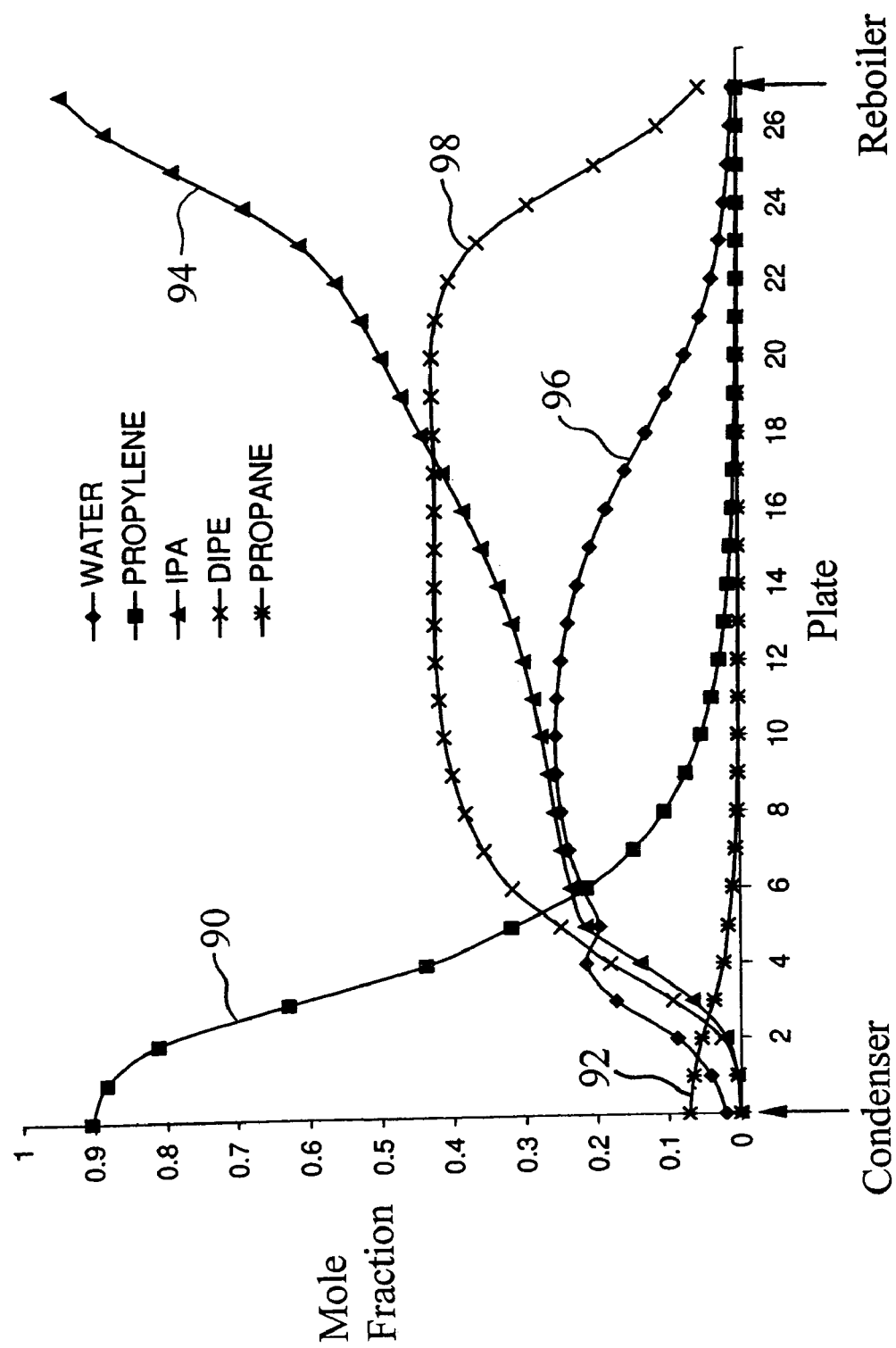
FIG. 7 is a profile of the steady state composition of the components of the reaction mixture during hydration of propene to isopropanol at an operating pressure of 4 megaPascals in the catalytic distillation column having two catalyst beds shown in FIG. 4.

The profile of the reaction mixture by stages is illustrated in FIG. 7 for use of catalytic distillation column 112, and condenser 73 and reboiler 83, as illustrated in FIG. 3. The effluent stream fed to reboiler 83 and to first volatiles line 80 comprises only unreacted propene, the mole fraction of which is shown as plot line 90 in FIG. 7, and propane, shown as plot line 92, a contaminant in propene feed 44. Liquid product 66 collected via first product line 72 comprises over 99% isopropanol, shown as plot line 94, containing a very small amount of water, shown as plot line 96, and DIPE, shown as plot line 98. At stage 21 through stage 26 of the liquid product stripping zone at third portion 36 of interior cavity 30, substantially all water is volatilized as a volatile three-component azeotropic mixture with isopropanol and DIPE. At stage 6 through stage 21 the volatile three-component mixture of water, DIPE and isopropanol is returned to the vicinity of reaction zone at second portion 34, stage 3 through stage 5. In the rectification zone at first portion 32, substantially all isopropanol, water and DIPE are returned as heavier components from stage 1 and stage 2 into the reaction zone at second portion 34, stage 3 through stage 5.

It can be seen from FIGS. 6 and 7 that the process of the present invention affords advantages for manufacture of isopropanol when compared with conventional processes exemplified by the process illustrated in FIG. 5. The advantages include production of substantially anhydrous isopropanol as liquid product, and less complex equipment and hence less costly capital and operation costs for the process.

It can be seen by comparison of FIG. 6 with FIG. 7 that operation of the process of the present invention for production of isopropanol at a pressure about 2 megaPascals is even more advantageous than operation of said process at a pressure about 4 megaPascals. The liquid product produced at the operating pressure about 2 megaPascals, illustrated in FIG. 6, is more anhydrous and contains considerably less DIPE as a contaminant than the corresponding product produced at the operating pressure about 4 megaPascals, illustrated in FIG. 7.

It can be seen by comparison of Example 3 with Example 1 and by comparison of Example 4 with Example 2 that operation of the process of the present invention for production of isopropanol using catalytic distillation column 112 having two spaced apart catalyst beds 140 and 240 has advantages over operation of said process using catalytic distillation column 12 having single catalyst bed 40. The advantages include using a lower molar ratio of propene to water, thereby having the beneficial effect of reducing the cost of purifying and recycling unreacted propene by reducing the amount of unreacted propene recovered from stage 1.

Example 5

Figure 13:
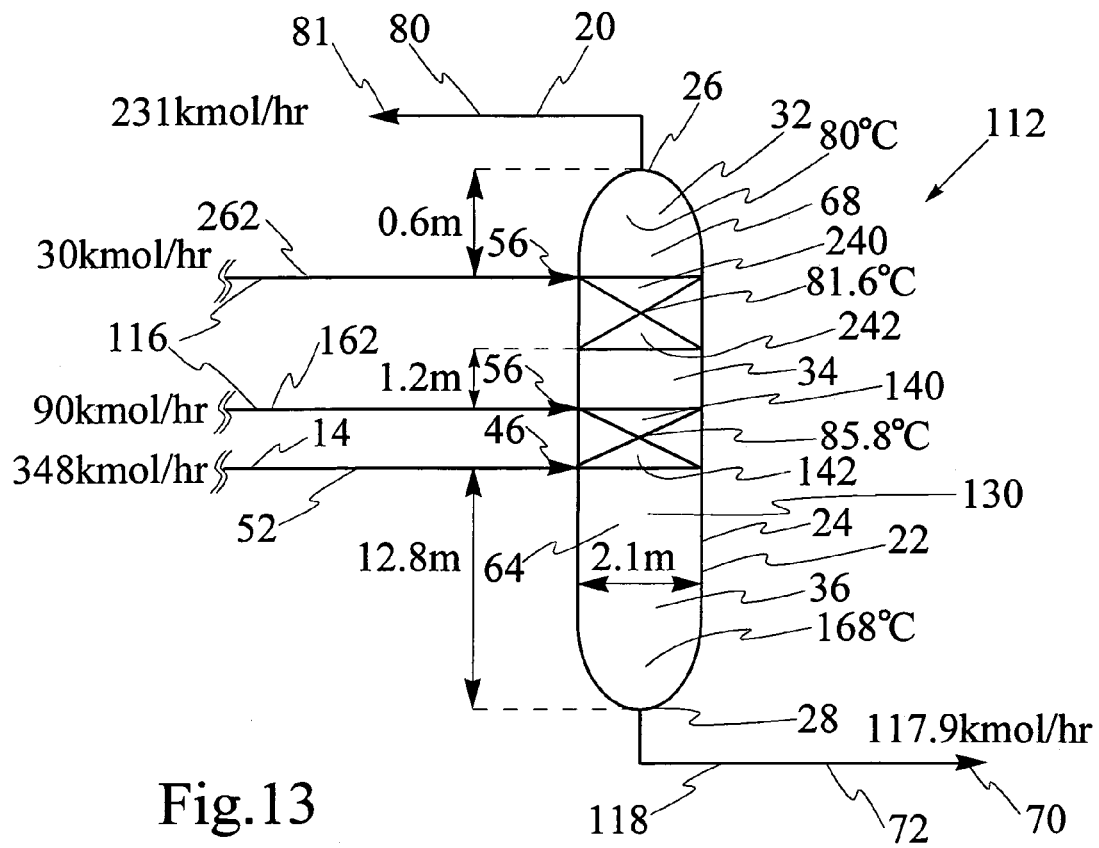
FIG. 13 is a schematic diagram showing the dimensions of the catalytic distillation column having two catalyst beds shown in FIG. 4, the temperatures at four positions, and the flow rates of the feed and exit streams for hydration of isobutene to tertiary butanol at a pressure of 1.2 megaPascals.

Referring to FIG. 13, catalytic distillation column 112 having substantially the same design and size as in Example 3 has been used for hydration of isobutene to tertiary butanol at a pressure of 1.2 megaPascals. The computer model has been used to determine that the temperatures at stage 1, stage 26, at first catalyst bed at stage 5 and at second catalyst bed at stage 2 are respectively 80° C., 168° C., 85.8° C. and 81.6° C., as illustrated. The molar feed rates for isobutene and water and the recovery rates for isobutene and tertiary butyl ether are each illustrated as values in kilomoles per hour. Isobutene conversion is 33.6%, water conversion is in excess of 99%, and the purity of the tertiary butanol stream is over 99.9% under these operating conditions.

Figure 8:
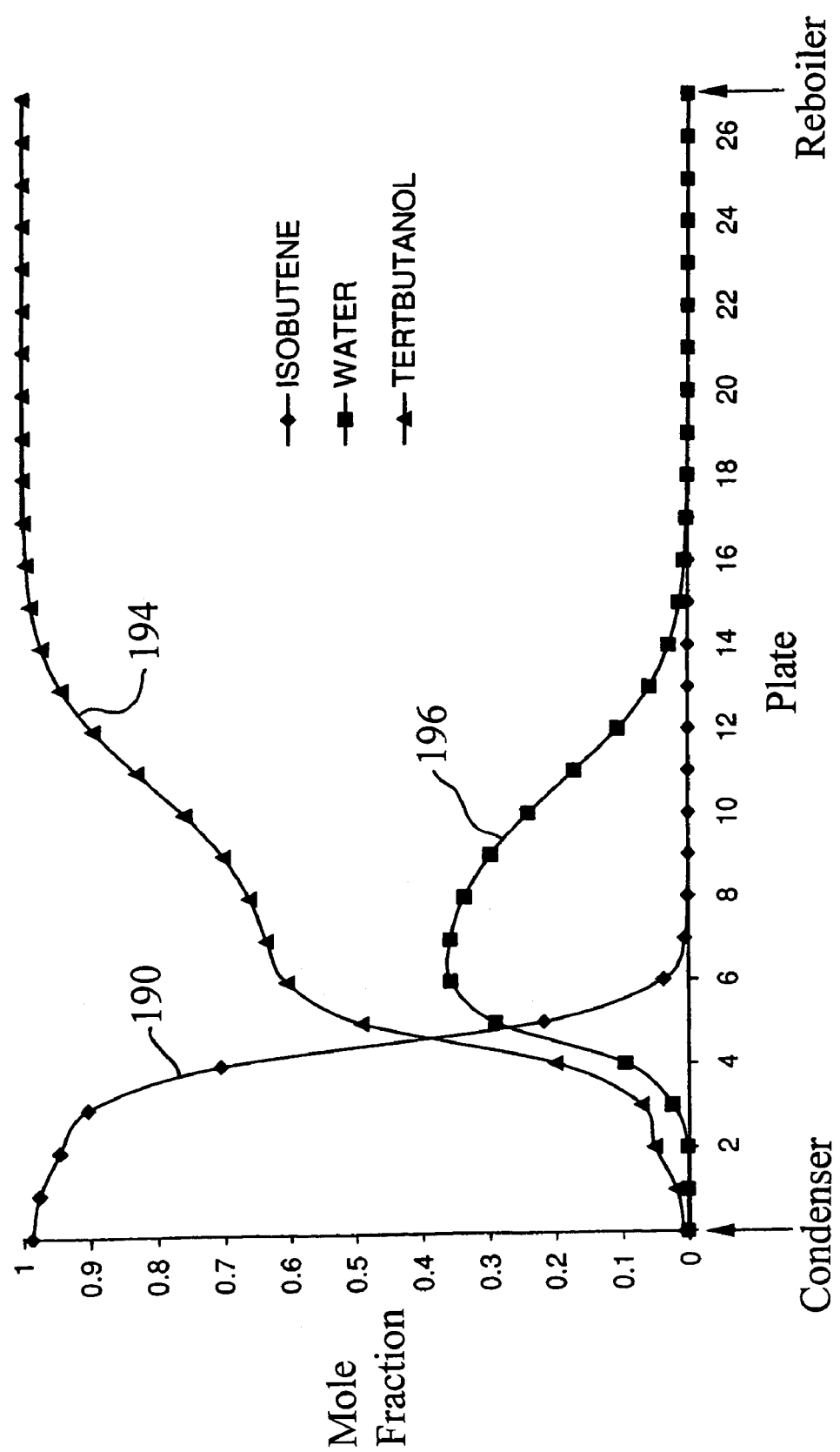
FIG. 8 is a profile of the steady state composition of the components of the reaction mixture during hydration of isobutene to tertiary butanol at an operating pressure of 1.2 megaPascals in the catalytic distillation column having two catalyst beds shown in FIG. 4.

The profile of the reaction mixture by stages is illustrated in FIG. 8 for use of catalytic distillation column 112, and condenser 73 and reboiler 83, as illustrated in FIG. 3. The effluent stream fed to reboiler 83 and to first volatiles line 80 comprises only unreacted isobutene, the mole fraction of which is shown as plot line 190 in FIG. 8. It will be recognized that isobutane and other contaminants may be present in the isobutene feed. In the present Example the feed is pure isobutene, and said contaminants are not included. Liquid product 66 collected via first product line 72 comprises over 99% tertiary butanol, shown as plot line 194, containing a very small amount of water, shown as plot line 96. It has been found that tertiary butanol is substantially free of di-tertiary ether as a by-product when isobutene is catalytically hydrated using an acidic cation exchange resin as catalyst in a batch process (Odioso et al., *Industrial and Engineering Chemistry*, March 1961, Volume 53 (3), pages 209–211). Similarly, it has been shown that hydration of linear butenes to 2-butanol over an acidic cation exchange resin as catalyst produces no measurable amounts of di-secondary butyl ether as a by-product. Consequently, production of di-tertiary butyl ether as a by-product has been excluded from the model of the present Example. At stage 6 through stage 26 of the liquid product stripping zone at third portion 36 of interior cavity 30, substantially all water is volatilized as a volatile two-component azeotropic mixture with tertiary butanol and is returned to the vicinity of reaction zone at second portion 34, at stage 2 through stage 5. In the rectification zone at first portion 32, at stage 1, substantially all tertiary butanol and water are returned as heavier components from stage 1 into the reaction zone at second portion 34, stage 2 through stage 5.

It can be seen from FIG. 8 that the process of the present invention affords advantages for manufacture of tertiary butanol when compared with conventional processes, including production of substantially anhydrous tertiary butanol as liquid product, and less complex equipment and hence less costly capital and operation costs for the process.

The process of the second aspect of present invention will now be illustrated using the following non-limiting Examples. In the Examples, the process described and the data obtained have been modeled using the commercially available computer program ASPENPLUS, with MESH equations and the UNIFAC method. The results have been confirmed by experiment using the AMBERLIST series of acidic cation exchanged resins or SILICALITE as catalyst 50 in laboratory scale equipment.

In the Examples the positions within catalytic distillation column 20 are identified as numbered stages: stage 1 is a distillation stage immediately below top 36. Further stages are then numbered sequentially to a last stage adjacent base 38.

Example 6

Figure 17:
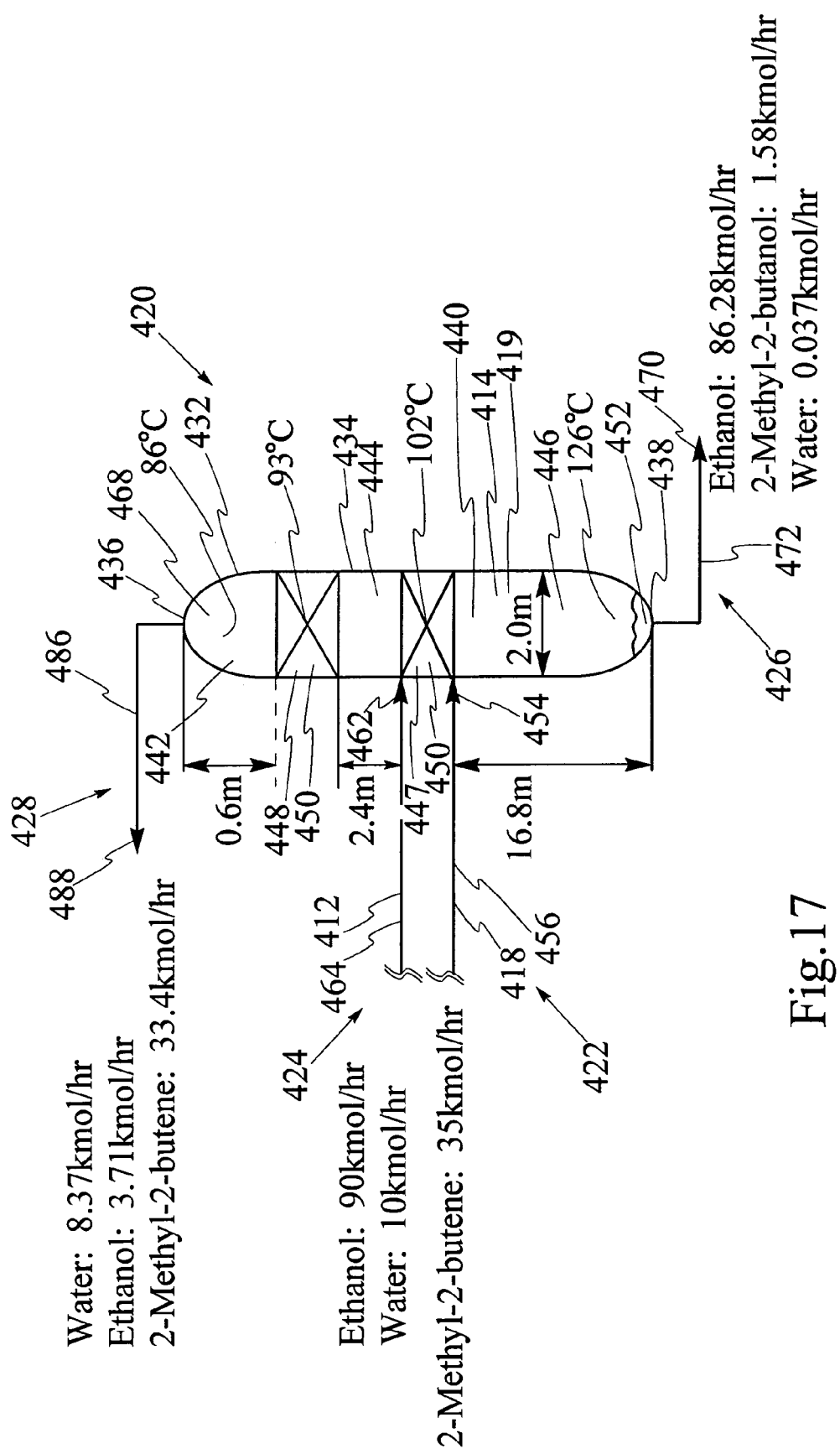
FIG. 17 is a schematic diagram showing the dimensions of the catalytic distillation column having two catalyst beds shown in FIG. 14, the temperatures at four positions, and the flow rates of the feed and exit streams for recovery of ethanol from an azeotropic mixture containing water by hydration of 2-methyl-2-butene at an operating pressure of 0.5 megaPascals.

Referring to FIGS. 14, 15 and 17, catalytic distillation column 420 having two spaced apart catalyst beds 447, 448 has been used for recovery of ethanol by reaction of 2-methyl-2-butene with the water content of a near azeotropic mixture 12 comprising 90% ethanol and 10% water at a pressure of 0.5 megaPascals. The computer model was run for catalytic distillation column 420 having the dimensions illustrated in FIG. 17. First portion 442 of interior cavity has one stage for rectification of volatiles. Second portion 444 contains lower catalyst bed 447 at stage 7 and upper catalyst bed 448 at stage 2, lower catalyst bed 447 and upper catalyst bed 448 being spaced apart by stage 3 through stage 6. Third portion 446 comprises stage 8 through stage 34, for stripping a liquid mixture of ethanol and 2-methyl-2-butanol from the reaction mixture. The temperatures at stage 1, stage 34, at lower catalyst bed 447 at stage 7 and at upper catalyst bed 448 at stage 2 respectively are 86° C., 126° C., 102° C. and 93° C., as illustrated. The pressure used is 0.5 Mpa, and the distillate rate is 45.5 kmol/h The molar feed rates for 2-methyl-2-butene and azeotropic mixture 412, and the recovery rates for ethanol, 2-methyl-2-butanol and unreacted 2-methyl-2-butene are each illustrated as values in kilomoles per hour. 2-Methyl-2-butene conversion is 4.5% and water conversion is over 12%. The alcohol content of liquid product 52 is over 99.9% under these operating conditions, with the balance being water (0.04%).

Figure 16:
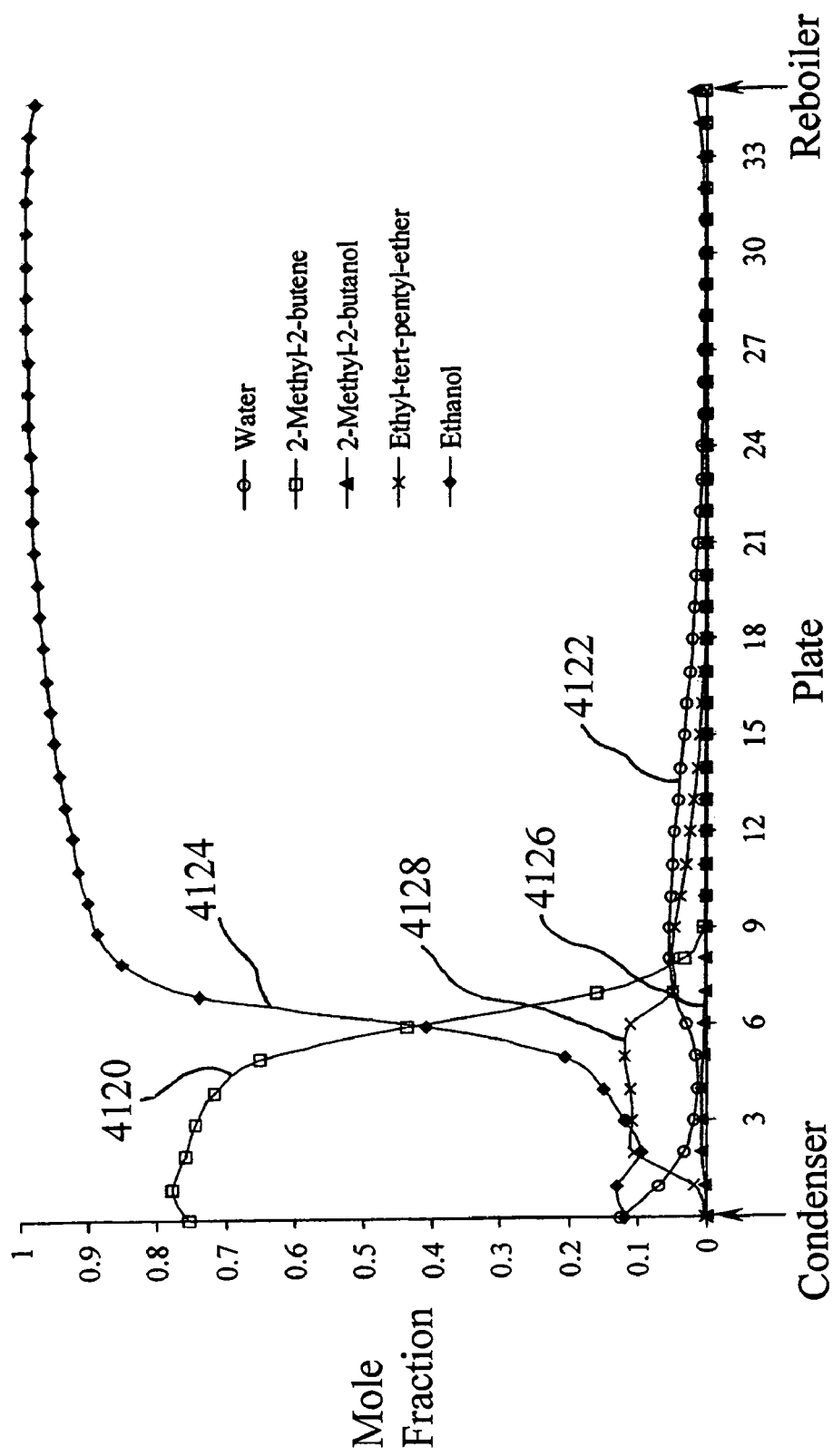
FIG. 16 is a profile of the composition of the components of the reaction mixture during the recovery of substantially anhydrous ethanol from an azeotropic mixture with water by the hydration of 2-methyl-2-butene at an operating pressure of 0.5 megaPascals, in the catalytic distillation column shown in FIG. 14.

The profile of the reaction mixture by stages is illustrated in FIG. 16 for use of catalytic distillation column 412, and condenser 490 and reboiler 474, as illustrated in FIG. 15. The effluent stream fed to condenser 490 and to first volatiles line 486 comprises mainly unreacted 2-methyl-2-butene, the mole fraction of which is shown as plot line 4120 in FIG. 16, unreacted water, shown as plot line 4122, and ethanol, shown as plot line 4124. Liquid product 452 collected via first product line 472 comprises over 99% alcohols: ethanol shown as plot line 4124 and 2-methyl-2-butanol shown as plot line 4126, containing a very small amount of water, plot line 4122. Under the reaction conditions of the present example, all di-(2-methyl-2-butyl) ether, plot line 4128, formed is in equilibrium with water, 2-methyl-2-butanol and 2-methyl-2-butene, and is retained predominantly within the reaction mixture between stage 2 and stage 18. At stage 1 through stage 27, substantially all water is volatilized as a mixture with ethanol and 2-methyl-2-butanol and is returned to the vicinity of reaction zone at second portion 434, stage 2 through stage 7. In the rectification zone at first portion 432, substantially all ethanol, water and 2-methyl-2-butanol are returned as heavier components from stage 1 into the reaction zone at second portion 434.

Ethanol and 2-methyl-2-butanol are readily separated by distillation in column 4108, as illustrated in FIG. 14.

Example 7

The equipment used in Example 7 is the same as that used in Example 6. The difference is that the operating conditions have been changed, resulting in differences in the composition of the product streams.

The feed rate of azeotropic mixture 412 is 90 kmol/h ethanol 414 and 10 kmol/h water 416. The feed rate of 2-methyl-2-butene 418 is 35 kmol/h. The temperatures at stage 1, adjacent top 436, at stage 34, adjacent base 438, at upper catalyst bed 448 at stage 2 and at lower catalyst bed 447 at stage 7 are 86° C., 125° C., 93° C. and 99° C., respectively. The pressure used is 0.5 MPa, and the distillate rate is 40.5 kmol/h. When first embodiment of equipment 410 is operated using these conditions and feed rates, the compositions of the product streams are as follows. Liquid 452 recovered at base 438 of column 20 comprises primarily ethanol (83 kmol/h), 2-methyl-2-butanol (1.9 kmol/h), ethyl (2-methyl-2-butyl) ether (3.2 kmol/h), and water (1.06 kmol/h). Volatiles 468 recovered from top 436 of column 420 include primarily 2-methyl-2-butene (29.9 kmol/h), ethanol (3.6 kmol/h), and water (7.0 kmol/h).

A comparison of Example 7 with Example 6 shows that operation of the present process under the conditions for Example 7 produces a liquid product 452 that contains a significant amount of ethyl (2-methyl-2-butyl) ether in contrast to the conditions of Example 6.

Example 8

Referring to FIG. 18, catalytic distillation column 520 having a total of 38 stages has been used for recovery of ethanol by reaction of 2-methyl-2-butene with the water content of a near azeotropic mixture 412 comprising 90% ethanol and 10% water at a pressure of 0.5 megaPascals. Catalytic distillation column 520 has two spaced apart catalyst beds 447, 448. Second liquid product recovery system 502 withdraws ethanol-rich liquid from a distillation plate at stage 30. Upper catalyst bed 448 is at stage 2 and lower catalyst bed 447 is at stage 7. The operating conditions for Example 8 are otherwise similar to the operating conditions for Example 6.

Azeotropic mixture 412 is fed at a rate of 90 kmol/h ethanol and 10 kmol/h water. He feed rate of 2-methyl-2-butene is 35 kmol/h. The temperatures at stage 1, adjacent top 436, at stage 34, adjacent base 438, upper catalyst bed at stage 2 and at lower catalyst bed at stage 7 are 86° C. 128° C. 93° C., and 104° C., respectively.

When second embodiment of equipment 500 is operated under these conditions and flow rates, the liquid product 452 comprises primarily ethanol (5.9 kmol/h) and 2-methyl-2-butanol (1.00 kmol/h). Volatiles 468 comprise primarily 2-methyl-2-butene (33.4 kmol/h), water (8.3 kmol/h), and ethanol (3.7 kmol/h). The liquid mixture 506 withdrawn as a side stream through take off line 504 comprises ethanol (80.3 kmol/h), 2-methyl-2-butanol (0.57 kmol/h) and water (0.10 kmol/h).

A comparison of Example 8 with Example 6 shows that inclusion of take off line 504 as second liquid product recovery system 502 allows recovery of liquid mixture 506 having a composition with 99% mole fraction ethanol, and minor amounts of impurities. The water content of liquid mixture 506 can be removed by distillation of an azeotropic mixture of the water with a minor portion of the ethanol. Ethanol can be recovered free from 2-methyl-2-butanol by distillation, with loss of a minor portion of the ethanol as a component of the residue.

It can be seen from FIGS. 16 through 18 that the process of the present invention affords advantages for recovery of ethanol from azeotropic mixtures containing water when compared with conventional processes exemplified by the process illustrated in FIG. 5. The advantages include production of substantially anhydrous ethanol, concurrent production of a useful higher molecular weight alcohol as a product, and less complex equipment and hence less costly capital and operation costs for the process. The higher molecular weight alcohol may be recovered as a useful mixture with ethanol, such as a solvent or an automotive fuel additive, or as a separate product stream, as illustrated in the Examples.

The invention claimed:

1. A process for reducing the water content of a starting feed stream comprising an azeotropic mixture of a first alcohol and water, comprising:

(a) effecting a hydration reaction of the water content of the feed stream with an olefin, wherein the olefin is hydrated to a corresponding second alcohol, the second alcohol being selected from the group consisting of the same alcohol as the first alcohol, an alcohol readily separable from the first alcohol by a distillation procedure, and an alcohol forming a useful mixture when mixed with the first alcohol, the hydration reaction of the olefin being conducted in the presence of a solid phase olefin hydration catalyst, the temperature and the pressure of the hydration reaction being selected so that the olefin is largely in the vapour phase and the first alcohol and the second alcohol are each largely in a liquid phase, the olefin being in a molar excess when compared with the water content of the feed stream, and (b) continuously removing the first alcohol and the second alcohol as a substantially anhydrous liquid mixture.

2. A process according to claim 1, wherein the catalyst has hydrophobic properties.

3. A process according to claim 2, wherein step (a) the reaction is performed at a temperature and pressure selected so that the rate of hydration reaction is high, and conversion of the olefin to the corresponding second alcohol is favored over conversion to the corresponding ether.

4. A process according to claim 3, wherein the reaction in step (a) is effected by catalytic distillation.

5. A process according to claim 3, wherein the second alcohol is different from the first alcohol.

6. A process according to claim 4, wherein the second alcohol is of a higher molecular weight than the first alcohol.

7. A process according to claim 3, wherein the first alcohol is ethanol, the added olefin has at least about five carbon atoms.

8. A process according to claim 3, wherein the first alcohol is ethanol, and the olefin is 2-methyl-2-butene.

9. A process according to claim 3, wherein the catalyst is a silicate, having a highly regular crystallographic structure characterized by a large surface area, and interconnected cavities within the regular structure.

10. A process for reducing the water content of a starting feed stream comprising an azeotropic or near azeotropic mixture of a first alcohol and water, comprising (a) effecting a hydration reaction of the water content of the feed stream with an olefin, wherein the olefin is hydrated to a corresponding second alcohol, the second alcohol being selected from the group consisting of the same alcohol as the first alcohol, an alcohol readily separable from the first alcohol by a distillation procedure, and an alcohol forming a useful mixture when mixed with the first alcohol, the hydration reaction of the olefin being conducted in the presence of a solid phase hydration catalyst, the temperature and the pressure of the hydration reaction being selected so that the olefin is largely in the vapour phase and the first alcohol and the second alcohol are each largely in a liquid phase, the olefin being in a molar excess when compared with the water content of the feed stream, the hydration reaction being conducted by catalytic distillation in a distillation column in the presence of a solid phase hydrophobic olefin hydration catalyst, the catalyst being disposed within the column in a plurality of spaced apart catalytic beds, the olefin and the feed stream being continuously fed to the column: and (b) continuously removing the first alcohol and the second alcohol as substantially anhydrous liquid mixture.

11. A process according to claim 10, wherein step a) the temperature and pressure are selected so that the rate of the hydration reaction is high, conversion of the olefin to the corresponding second alcohol is favored over conversion to the corresponding ether, and etherification of the olefin does not occur to a measurable degree.

12. A process according to claim 10, wherein step (a) the pressure is 0.25–2.5 and the temperature is 70–180° C.

13. A process according to claim 12, wherein the silicate is sulfated.

14. A process according to claim 11, wherein the catalyst is a silicate, having a highly regular crystallographic structure characterized by a large surface area, and interconnected cavities within the regular structure.

15. A process according to claim 14, wherein the silicate is sulfated.

* * * * *